United States Patent
Kotou et al.

(10) Patent No.: US 10,374,256 B2
(45) Date of Patent: Aug. 6, 2019

(54) NONAQUEOUS ELECTROLYTE SOLUTION, ELECTRICITY STORAGE DEVICE USING SAME, AND PHOSPHONOFORMIC ACID COMPOUND USED IN SAME

(71) Applicant: UBE INDUSTRIES, LTD., Ube-shi (JP)

(72) Inventors: Yuichi Kotou, Ube (JP); Masahide Kondo, Ube (JP)

(73) Assignee: UBE INDUSTRIES, LTD., Ube-shi (JP)

(*) Notice: Subject to any disclaimer, the term of this patent is extended or adjusted under 35 U.S.C. 154(b) by 421 days.

(21) Appl. No.: 15/104,419

(22) PCT Filed: Aug. 7, 2014

(86) PCT No.: PCT/JP2014/070895
§ 371 (c)(1),
(2) Date: Jun. 14, 2016

(87) PCT Pub. No.: WO2015/093091
PCT Pub. Date: Jun. 25, 2015

(65) Prior Publication Data
US 2016/0315351 A1    Oct. 27, 2016

(30) Foreign Application Priority Data

Dec. 19, 2013 (JP) .................. 2013-262933
Mar. 25, 2014 (JP) .................. 2014-061075

(51) Int. Cl.
*H01M 10/0567* (2010.01)
*H01G 11/64* (2013.01)
(Continued)

(52) U.S. Cl.
CPC ....... *H01M 10/0567* (2013.01); *C07F 9/4065* (2013.01); *C07F 9/4078* (2013.01);
(Continued)

(58) Field of Classification Search
CPC ......... H01M 10/0567; H01M 10/0568; H01M 10/0569; H01M 10/052; H01M 10/0525;
(Continued)

(56) References Cited

U.S. PATENT DOCUMENTS

| | | | |
|---|---|---|---|
| 2010/0035147 A1 | 2/2010 | Kotato et al. | |
| 2012/0156557 A1 | 6/2012 | Kotato et al. | |

(Continued)

FOREIGN PATENT DOCUMENTS

| | | | |
|---|---|---|---|
| CN | 103904359 | * | 7/2014 |
| JP | 10-189039 A | | 7/1998 |

(Continued)

OTHER PUBLICATIONS

International Search Report dated Oct. 28, 2014 in PCT/JP2014/070895 filed on Aug. 7, 2014.

*Primary Examiner* — Laura Weiner
(74) *Attorney, Agent, or Firm* — Oblon, McClelland, Maier & Neustadt, L.L.P.

(57) ABSTRACT

The present invention provides a nonaqueous electrolytic solution capable of suppressing worsening of heat stability of a negative electrode and improving safety of an energy storage device while maintaining high-load charging and discharging cycle properties at a high temperature, an energy storage device using the same, and a phosphonoformic acid compound to be used for the same. The nonaqueous electrolytic solution having an electrolyte salt dissolved in a nonaqueous solvent contains 0.001 to 5% by mass of at least one selected from a phosphonoformic acid compound having at least one carbon-carbon unsaturated bond, which is represented by the following general formula (I), and a phosphonoformic acid compound having a carbon-carbon unsaturated bond or two phosphonocarbonyl groups, which is represented by the following general formula (II).

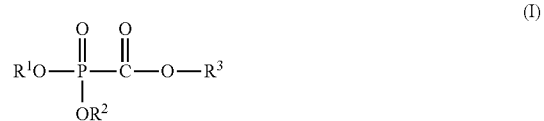

In the formula (I), each of $R^1$ to $R^3$ is an aliphatic organic group, provided that at least one of $R^1$ to $R^3$ represents a carbon-carbon unsaturated bond-containing aliphatic organic group.

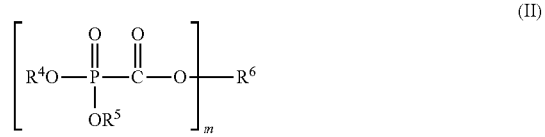

In the formula (II), each of $R^4$ and $R^5$ represents an alkyl group, a cycloalkyl group, or an aryl group, and $R^4$ and $R^5$ may be bonded to each other to form a ring structure. m represents 1 or 2; when m is 1, then $R^6$ represents an aryl group; when m is 2, then $R^6$ represents an alkylene group, an alkenylene group, or an alkynylene group; and a part of hydrogen atoms of $R^4$ to $R^6$ may be substituted with a halogen atom.

15 Claims, No Drawings

(51) Int. Cl.

| | | |
|---|---|---|
| H01M 10/0568 | (2010.01) | |
| H01M 10/0569 | (2010.01) | |
| H01M 10/052 | (2010.01) | |
| C07F 9/6571 | (2006.01) | |
| C07F 9/40 | (2006.01) | |
| H01G 11/46 | (2013.01) | |
| H01G 11/50 | (2013.01) | |
| H01M 2/16 | (2006.01) | |
| H01M 4/131 | (2010.01) | |
| H01M 4/133 | (2010.01) | |
| H01M 4/505 | (2010.01) | |
| H01M 4/525 | (2010.01) | |
| H01M 4/62 | (2006.01) | |
| H01M 4/66 | (2006.01) | |
| H01M 10/0525 | (2010.01) | |
| H01M 10/0585 | (2010.01) | |
| H01M 10/42 | (2006.01) | |
| H01M 4/04 | (2006.01) | |
| H01M 4/1391 | (2010.01) | |
| H01M 4/1393 | (2010.01) | |
| H01M 4/02 | (2006.01) | |

(52) U.S. Cl.
CPC ....... *C07F 9/657181* (2013.01); *H01G 11/46* (2013.01); *H01G 11/50* (2013.01); *H01G 11/64* (2013.01); *H01M 2/162* (2013.01); *H01M 2/1653* (2013.01); *H01M 4/131* (2013.01); *H01M 4/133* (2013.01); *H01M 4/505* (2013.01); *H01M 4/525* (2013.01); *H01M 4/623* (2013.01); *H01M 4/625* (2013.01); *H01M 4/661* (2013.01); *H01M 10/052* (2013.01); *H01M 10/0525* (2013.01); *H01M 10/0568* (2013.01); *H01M 10/0569* (2013.01); *H01M 10/0585* (2013.01); *H01M 10/4235* (2013.01); *H01M 4/043* (2013.01); *H01M 4/0404* (2013.01); *H01M 4/1391* (2013.01); *H01M 4/1393* (2013.01); *H01M 2004/027* (2013.01); *H01M 2004/028* (2013.01); *H01M 2220/20* (2013.01); *H01M 2220/30* (2013.01); *H01M 2300/0025* (2013.01); *H01M 2300/0042* (2013.01); *Y02E 60/13* (2013.01); *Y02T 10/7011* (2013.01); *Y02T 10/7022* (2013.01)

(58) Field of Classification Search
CPC ......... H01M 10/0585; H01M 10/4235; H01M 4/131; H01M 4/133; H01M 4/505; H01M 4/525; H01M 4/623; H01M 4/625; H01M 4/661; H01M 4/0404; H01M 4/043; H01M 4/1391; H01M 4/1393; H01M 2004/027; H01M 2004/028; H01M 2220/20; H01M 2220/30; H01M 2300/0025; H01M 2300/0042; Y02T 10/7022; Y02T 10/7011; Y02E 60/13

See application file for complete search history.

(56) References Cited

U.S. PATENT DOCUMENTS

| 2012/0264011 A1 | 10/2012 | Kotato et al. |
| 2014/0030610 A1 | 1/2014 | Abe et al. |

FOREIGN PATENT DOCUMENTS

| JP | 2009-70615 A | 4/2009 |
| WO | 2008/123038 A1 | 10/2008 |
| WO | 2012/141270 A1 | 10/2012 |
| WO | 2013/047747 A1 | 4/2013 |
| WO | 2013/168716 A1 | 11/2013 |

\* cited by examiner

NONAQUEOUS ELECTROLYTE SOLUTION, ELECTRICITY STORAGE DEVICE USING SAME, AND PHOSPHONOFORMIC ACID COMPOUND USED IN SAME

TECHNICAL FIELD

The present invention relates to a nonaqueous electrolytic solution capable of improving high-load charging and discharging cycle properties at a high temperature and heat stability and safety, an energy storage device using the same, and a phosphonoformic acid compound to be used for the same.

BACKGROUND ART

An energy storage device, especially a lithium secondary battery, has been widely used recently for a power source of an electronic device, such as a mobile telephone, a notebook personal computer, etc., and a power source for an electric vehicle or electric power storage. There is a high possibility that a battery mounted on such an electronic device or a vehicle is used at a high temperature in midsummer or in the environment warmed by the heat generation of the electronic device.

A lithium secondary battery is mainly constituted of a positive electrode and a negative electrode, each containing a material capable of absorbing and releasing lithium, and a nonaqueous electrolytic solution composed of a lithium salt and a nonaqueous solvent, and a carbonate, such as ethylene carbonate (EC), propylene carbonate (PC), etc., is used as the nonaqueous solvent.

In addition, a lithium metal, a metal compound capable of absorbing and releasing lithium (e.g., a metal elemental substance, a metal oxide, an alloy with lithium, etc.), and a carbon material are known as the negative electrode of the lithium secondary battery. In particular, a nonaqueous electrolytic solution secondary battery using, as the carbon material, a carbon material capable of absorbing and releasing lithium, for example, coke or graphite (e.g., artificial graphite or natural graphite), etc., is widely put into practical use.

Since the aforementioned negative electrode material stores and releases lithium and an electron at an extremely electronegative potential equal to the lithium metal, it has a possibility that a lot of solvents are subjected to reductive decomposition particularly at a high temperature, and a part of the solvent in the electrolytic solution is reductively decomposed on the negative electrode regardless of the kind of the negative electrode material, so that there were involved such problems that the movement of a lithium ion is disturbed due to deposition of a decomposed product or generation of a gas, thereby worsening battery characteristics, such as cycle properties particularly at a high temperature, etc., and further worsening heat stability of the negative electrode. Furthermore, it is known that a lithium secondary battery using a lithium metal or an alloy thereof, a metal elemental substance, such as tin, silicon, etc., or a metal oxide thereof as the negative electrode material may have a high initial battery capacity, but the battery capacity and the battery performance thereof, such as cycle properties, may be largely worsened particularly at a high temperature because the micronized powdering of the material may be promoted during cycles, which brings about accelerated reductive decomposition of the nonaqueous solvent, as compared with the negative electrode formed of a carbon material.

Meanwhile, since a material capable of absorbing and releasing lithium, which is used as a positive electrode material, such as $LiCoO_2$, $LiMn_2O_4$, $LiNiO_2$, $LiFePO_4$, etc., stores and releases lithium and an electron at an electropositive voltage of 3.5 V or more on the lithium basis, it is known that in an interface between the positive electrode material and the nonaqueous electrolytic solution, a decomposed product or a gas generated by local oxidative decomposition disturbs a desirable electrochemical reaction. There is a possibility that a lot of solvents are subjected to oxidative decomposition particularly at a high temperature, and a part of the solvent in the electrolytic solution is oxidatively decomposed on the positive electrode regardless of the kind of the positive electrode material, so that there was involved such a problem that the movement of a lithium ion is disturbed due to deposition of a decomposed product or generation of a gas, thereby worsening battery characteristics, such as cycle properties, etc.

Irrespective of the foregoing situation, the multifunctionality of electronic devices on which lithium secondary batteries are mounted is more and more advanced, and the electric power consumption tends to increase. The capacity of the lithium secondary battery is thus being much increased, and shortening of a charging time is demanded, too. But, in the case of repeating the charging and discharging cycle at such a high load, an absorbing reaction of a lithium ion in the negative electrode does not uniformly occur over the entirety of the negative electrode, and metallic lithium is apt to deposit on the negative electrode surface where the reaction is concentrated, whereby heat stability of the negative electrode is worsened, and also, a decomposition reaction of the electrolytic solution proceeds. For this reason, it is demanded to improve high-load charging and discharging cycle properties, heat stability of the negative electrode, and safety.

With respect to the safety, PTL 1 discloses a nonaqueous electrolytic solution composed of a nonaqueous solvent including a phosphoric acid ester compound, such as triethyl phosphonoacetate, etc., and an electrolyte and describes that the electrolytic solution exhibits self-fire extinguishing property.

In addition, PTL 2 discloses a nonaqueous electrolytic solution containing, as an additive, a phosphoric acid ester compound, such as triethyl phosphonoacetate, triethyl phosphonoformate, etc. and describes that the continuous charging characteristics and high-temperature storage properties are improved, and the gas generation can be suppressed.

PTL 3 describes that a lithium secondary battery using a nonaqueous electrolytic solution including a phosphonoacetate compound, such as triethyl phosphonoacetate, etc., is capable of exhibiting high-temperature storage properties or suppressing swelling of the battery.

CITATION LIST

Patent Literature

PTL 1: JP-A 10-189039
PTL 2: WO 2008/123038
PTL 3: WO 2013/047747

SUMMARY OF INVENTION

Technical Problem

Problems to be solved by the present invention are to provide a nonaqueous electrolytic solution capable of suppressing worsening of heat stability of a negative electrode and improving safety of an energy storage device while maintaining high-load charging and discharging cycle properties at a high temperature, and also to provide an energy storage device using the same and a phosphonoformic acid compound to be used for the same.

Solution to Problem

The present inventors made extensive and intensive investigations regarding the performances of the nonaqueous electrolytic solutions of the aforementioned conventional technologies.

According to PTL 1, though the self-fire extinguishing property of the electrolytic solution is improved by using an excess of triethyl phosphonoacetate, an improvement of the high-load charging and discharging cycle properties and an improvement of the heat stability of a negative electrode are not disclosed at all.

In addition, though the nonaqueous electrolytic solutions of PTLs 2 and 3 could suppress the gas generation or swelling, in fact, it may not be said that they were satisfactory against the problem to improve the electrochemical characteristics at a high temperature.

PTL 3 discloses, as the phosphonoacetic acid ester, compounds extending over a wide range, inclusive of phosphonoacetic acid esters, phosphonoformic acid esters, phosphonopropionic acid esters, phosphonobutanoic acid esters, and the like, and suggests that a part of the foregoing compounds may be substituted with an alkenyl group or an alkynyl group. However, PTL 3 neither specifically describes any compound in which a part of the phosphonoformic acid ester is substituted with an alkenyl group or an alkynyl group nor provides any working example.

In the light of the above, PTLs 1 to 3 do not provide any disclosure at all against problems to improve the high-load charging and discharging cycle properties and further to improve the heat stability of a negative electrode when a temperature of the battery abnormally increases due to heating by improper use, overcharge, internal short circuit by a foreign matter or shock, or the like.

Then, in order to solve the aforementioned problems, the present inventors made extensive and intensive investigations. As a result, it has been found that in a nonaqueous electrolytic solution having an electrolyte salt dissolved in a nonaqueous solvent, by adding a small amount of a phosphonoformic acid compound having a certain specified substituent in the nonaqueous electrolytic solution, the high-load charging and discharging cycle properties at a high temperature and further the heat stability of a negative electrode can be improved, and the safety of an energy storage device inclusive of a lithium secondary battery can be improved, leading to accomplishment of the present invention.

Specifically, the present invention provides the following (1) to (3).
(1) A nonaqueous electrolytic solution having an electrolyte salt dissolved in a nonaqueous solvent, the nonaqueous electrolytic solution containing 0.001 to 5% by mass of at least one selected from a phosphonoformic acid compound having at least one carbon-carbon unsaturated bond, which is represented by the following general formula (I), and a phosphonoformic acid compound having a carbon-carbon unsaturated bond or two phosphonocarbonyl groups, which is represented by the following general formula (II).

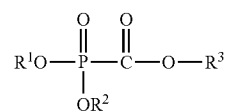

(I)

In the formula, each of $R^1$ to $R^3$ independently represents an aliphatic organic group having 1 to 5 carbon atoms, provided that at least one of $R^1$ to $R^3$ represents a carbon-carbon unsaturated bond-containing aliphatic organic group having 2 to 5 carbon atoms.

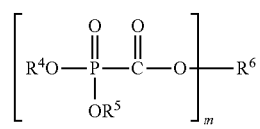

(II)

In the formula, each of $R^4$ and $R^5$ independently represents an alkyl group having 1 to 6 carbon atoms, a cycloalkyl group having 3 to 6 carbon atoms, or an aryl group having 6 to 12 carbon atoms, and $R^4$ and $R^5$ may be bonded to each other to form a ring structure. m represents 1 or 2; when m is 1, then $R^6$ represents an aryl group having 6 to 12 carbon atoms; when m is 2, then $R^6$ represents an alkylene group having 2 to 6 carbon atoms, an alkenylene group having 4 to 8 carbon atoms, or an alkynylene group having 4 to 8 carbon atoms; and a part of hydrogen atoms of $R^4$ to $R^6$ may be substituted with a halogen atom.
(2) An energy storage device including a positive electrode, a negative electrode, and a nonaqueous electrolytic solution having an electrolyte salt dissolved in a nonaqueous solvent, the nonaqueous electrolytic solution containing 0.001 to 5% by mass of at least one selected from a phosphonoformic acid compound having at least one carbon-carbon unsaturated bond, which is represented by the foregoing general formula (I), and a phosphonoformic acid compound having a carbon-carbon unsaturated bond or two phosphonocarbonyl groups, which is represented by the foregoing general formula (II).
(3) A phosphonoformic acid compound having at least one alkynyl group, which is represented by the following general formula (III).

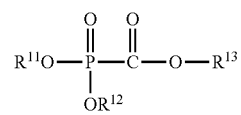

(III)

In the formula, each of $R^{11}$ to $R^{13}$ independently represents an aliphatic organic group having 1 to 5 carbon atoms, provided that at least one of $R^{11}$ to $R^{13}$ represents an alkynyl group having 3 to 5 carbon atoms.

Advantageous Effects of Invention

In accordance with the present invention, it is possible to provide a nonaqueous electrolytic solution capable of suppressing worsening of heat stability of a negative electrode and improving safety of an energy storage device inclusive of a lithium secondary battery while maintaining high-load charging and discharging cycle properties at a high temperature, an energy storage device using the same, such as a lithium battery, etc., and a phosphonoformic acid compound to be used for the same.

In addition, since the nonaqueous electrolytic solution of the present invention forms a surface film with high heat stability even on a negative electrode made of lithium metal or the like in a lithium primary battery, even when the lithium primary battery is stored at a high temperature, a lowering of the capacity can be suppressed. For that reason, the nonaqueous electrolytic solution of the present invention is useful as a nonaqueous electrolytic solution not only for a lithium secondary battery but also for a lithium primary battery.

DESCRIPTION OF EMBODIMENTS

[Nonaqueous Electrolytic Solution]

The nonaqueous electrolytic solution of the present invention is concerned with a nonaqueous electrolytic solution having an electrolyte salt dissolved in a nonaqueous solvent, the nonaqueous electrolytic solution containing 0.001 to 5% by mass of at least one selected from a phosphonoformic acid compound having at least one carbon-carbon unsaturated bond, which is represented by the foregoing general formula (I), and a phosphonoformic acid compound having a carbon-carbon unsaturated bond or two phosphonocarbonyl groups, which is represented by the foregoing general formula (II).

Although the reasons why the nonaqueous electrolytic solution of the present invention is able to greatly improve the cycle properties at a high load and further the heat stability of a negative electrode when the temperature abnormally increases are not always elucidated yet, the following may be considered.

In the phosphonoformic acid compound of the present invention, two electron attractive groups, namely an $(RO)_2P(=O)$ group and a $C(=O)O—$ group, are directly bonded to each other, and therefore, it may be considered that the phosphonoformic acid compound of the present invention is likely reduced, so that its decomposition quickly proceeds on the negative electrode. Here, the compound represented by the general formula (I) has an aliphatic organic group having at least one carbon-carbon unsaturated bond, and therefore, it may be considered that a minute and firm surface film is formed.

In the compound represented by the general formula (II), when m is 1, the compound also has an aryl group having a carbon-carbon unsaturated bond, and it may be considered that, similarly to the case as in the general formula (I), a surface film is formed.

Furthermore, in the compound represented by the general formula (II), when m is 2, since the compound has two phosphonocarbonyl groups $[(RO)_2P(=O)—C(=O)—$ groups], it is expected that the compound is more likely reduced, and even when the two phosphonocarbonyl groups are connected with each other via an alkylene group, it may be considered that a surface film is formed via the carbon-carbon unsaturated bond during the decomposition process through the same mechanism.

It is conjectured that not only such a surface film is minute and firm, but also the surface is coated with a phosphate skeleton derived from the $(RO)_2P(=O)$ group, and as a result, it may be considered that even on high-load charging and discharging, the surface film has flexibility to such an extent that it does not disturb the permeation of a lithium ion and contributes to an improvement of the heat stability.

Such an effect is an effect that cannot be achieved by triethyl phosphonoformate not having a carbon-carbon unsaturated bond, or triethyl phosphonoacetate in which the $(RO)_2P(=O)C—$ group and the $C(=O)O—$ group are not directly bonded to each other, and it may be considered that this effect is an effect peculiar to the present invention.

<Phosphonoformic Acid Compound Represented by General Formula (I)>

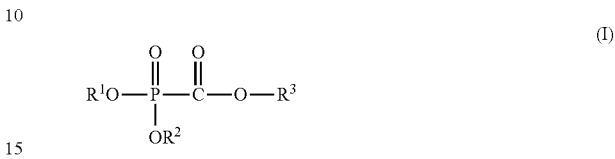

In the general formula (I), each of $R^1$ to $R^3$ independently represents an aliphatic organic group having 1 to 5 carbon atoms, provided that at least one of $R^1$ to $R^3$ represents a carbon-carbon unsaturated bond-containing aliphatic organic group having 2 to 5 carbon atoms.

The aliphatic organic group as referred to in the present specification means an aliphatic functional group constituted of an atom selected from a carbon atom, a hydrogen atom, a nitrogen atom, an oxygen atom, and a halogen atom. Specific examples thereof include an alkyl group, an alkenyl group, an alkynyl group, an alkoxy group, a nitrile group, an isocyanate group, an ether group, a carbonate group, a carbonyl group, and the like, and a hydrocarbon group, such as an alkyl group, an alkenyl group, an alkynyl group, etc., is preferred.

That is, the aliphatic organic group having 1 to 5 carbon atoms, which is represented by $R^1$ to $R^3$, is preferably an alkyl group having 1 to 5 carbon atoms, an alkenyl group having 2 to 5 carbon atoms, or an alkynyl group having 3 to 5 carbon atoms, and the carbon-carbon unsaturated bond-containing aliphatic organic group having 2 to 5 carbon atoms is preferably an alkenyl group having 2 to 5 carbon atoms or an alkynyl group having 3 to 5 carbon atoms.

When $R^1$ to $R^3$ are an alkyl group, suitable examples thereof include a straight-chain alkyl group, such as a methyl group, an ethyl group, an n-propyl group, an n-butyl group, an n-pentyl group, etc., and a branched alkyl group, such as an isopropyl group, a sec-butyl group, a tert-butyl group, etc. The carbon number of the aforementioned alkyl group is more preferably 1 to 3, and specifically, a methyl group, an ethyl group, or an n-propyl group is more preferred, and a methyl group or an ethyl group is still more preferred.

When $R^1$ to $R^3$ are an alkenyl group, suitable examples thereof include a straight-chain alkenyl group, such as a vinyl group, a 2-propenyl group, a 2-butenyl group, a 3-butenyl group, etc., and a branched alkenyl group, such as a 2-methyl-2-propenyl group, a 3-butene-2-yl group, a 2-methyl-3-butene-2-yl group, a 3-methyl-2-butenyl group, etc. The carbon number of the aforementioned alkenyl group is more preferably 2 or 3, and specifically, a vinyl group or a 2-propenyl group is more preferred, and a 2-propenyl group is still more preferred.

When $R^1$ to $R^3$ are an alkynyl group, suitable examples thereof include a straight-chain alkynyl group, such as a 2-propynyl group, a 2-butynyl group, a 3-butynyl group, a 2-pentynyl group, etc., and a branched alkynyl group, such as a 3-butyne-2-yl group, a 2-methyl-3-butyne-2-yl group, etc. The carbon number of the aforementioned alkynyl group is more preferably 3 or 4, and specifically, a 2-proynyl group or a 3-butynyl group is more preferred, and a 2-proynyl group is still more preferred.

In the general formula (I), at least one of $R^1$ to $R^3$ represents a carbon-carbon unsaturated bond-containing aliphatic organic group having 2 to 5 carbon atoms. $R^3$ is preferably an alkenyl group having 2 to 5 carbon atoms or an alkynyl group having 3 to 5 carbon atoms, and more preferably an alkynyl group having 3 to 5 carbon atoms. It is still more preferred that $R^3$ is an alkynyl group having 3 to 5 carbon atoms, and each of $R^1$ and $R^2$ is independently an alkyl group having 1 to 4 carbon atoms or an alkynyl group having 3 to 5 carbon atoms, and it is especially preferred that all of $R^1$ to $R^3$ are an alkynyl group having 3 to 4 carbon atoms.

As specific examples of the phosphonoformic acid compound having at least one carbon-carbon unsaturated bond, which is represented by the general formula (I), there are suitably exemplified the following compounds.

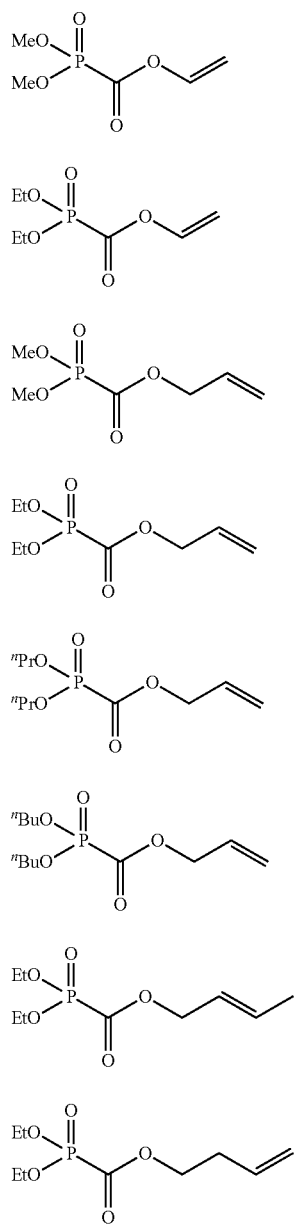

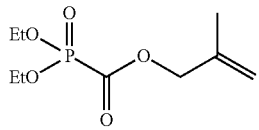

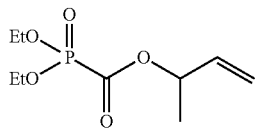

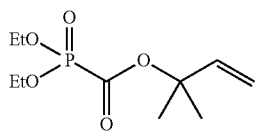

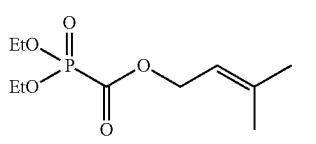

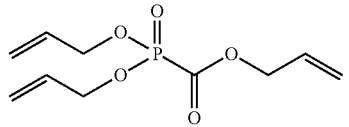

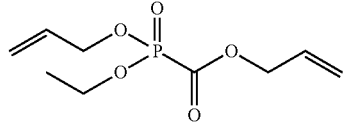

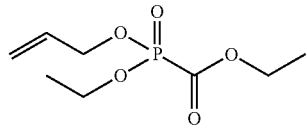

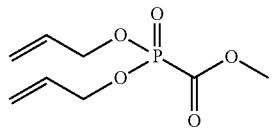

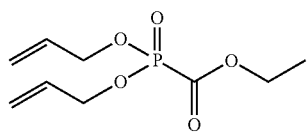

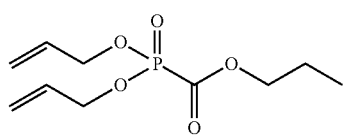

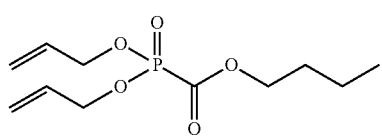

| | |
|---|---|
| 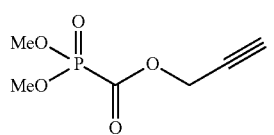 B1 | 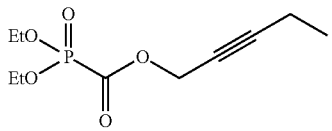 B11 |
| 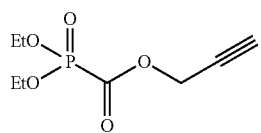 B2 | 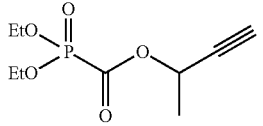 B12 |
| 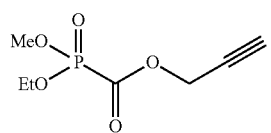 B3 | 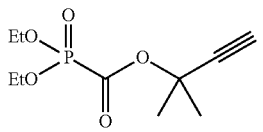 B13 |
| 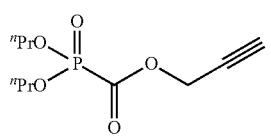 B4 | 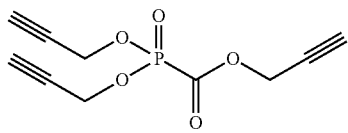 B14 |
| 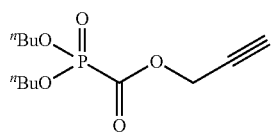 B5 | 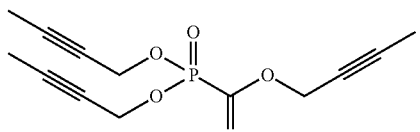 B15 |
| 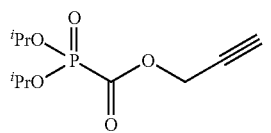 B6 | 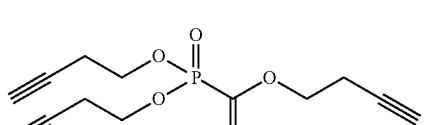 B16 |
| 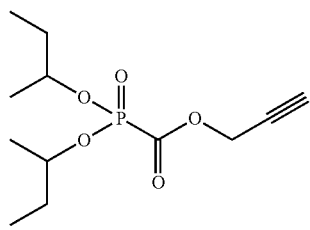 B7 | 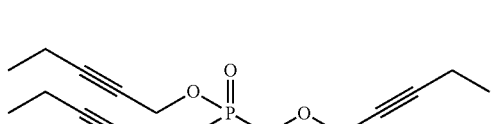 B17 |
| 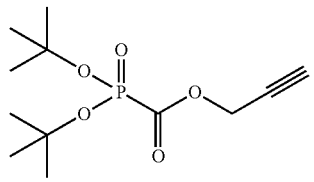 B8 | 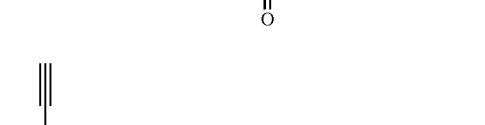 B18 |
| 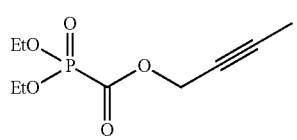 B9 | 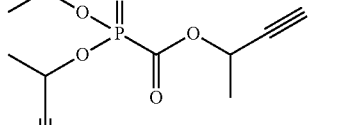 B19 |
| 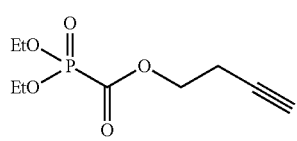 B10 | 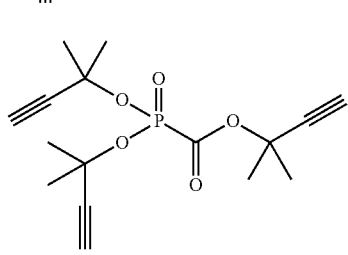 |

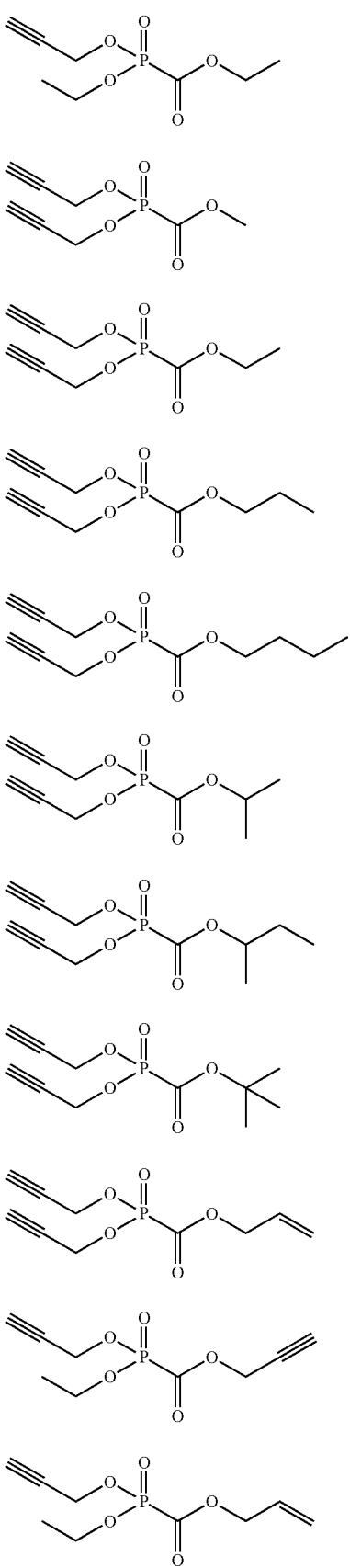

Among the aforementioned compounds, Compounds A1 to A14, B1 to B19, B29, and B32 are preferred; Compounds B1 to B19 are more preferred; one or more selected from 2-propynyl (dimethoxyphosphoryl)formate (Compound B1), 2-propynyl (diethoxyphosphoryl)formate (Compound B2), 2-propynyl (ethoxymethoxyphosphoryl)formate (Compound B3), 2-propynyl (dipropyloxyphosphoryl)formate (Compound B4), 2-propynyl (dibutyloxyphosphoryl)formate (Compound B5), 2-butynyl (diethoxyphosphoryl)formate (Compound B9), 2-pentynyl (diethoxyphosphoryl)formate (Compound B11), 3-butyne-2-yl (diethoxyphosphoryl)formate (Compound B12), 2-methyl-3-butyne-2-yl (diethoxyphosphoryl)formate (Compound B13), 2-propynyl (bis(2-propynyloxy)phosphoryl)formate (Compound B14), 2-butynyl (bis(2-butynyloxy)phosphoryl)formate (Compound B15), 2-pentynyl (bis(2-pentynyloxy)phosphoryl)formate (Compound B17), 3-butyne-2-yl (bis(3-butyne-2-yloxy)phosphoryl)formate (Compound B18), 2-methyl-3-butyne-2-yl (bis(2-methyl-3-butyne-2-yloxy)phosphoryl)formate (Compound B19), and 2-propynyl (ethoxy(2-propynyloxy)phosphoryl)formate (Compound B29) are preferred; and one or more selected from 2-propynyl (dimethoxyphosphoryl)formate (Compound B1), 2-propynyl (diethoxyphosphoryl)formate (Compound B2), 2-propynyl (bis(2-propynyloxy)phosphoryl)formate (Compound B14), 2-butynyl (bis(2-butynyloxy)phosphoryl)formate (Compound B15), and 3-butyne-2-yl (bis(3-butyne-2-yloxy)phosphoryl)formate (Compound B18) are especially preferred.

<Phosphonoformic Acid Compound Represented by General Formula (II)>

$$\left[ R^4O-\overset{\underset{\parallel}{O}}{\underset{OR^5}{P}}-\overset{\underset{\parallel}{O}}{C}-O \right]_m R^6 \quad (II)$$

In the general formula (II), each of $R^4$ and $R^5$ independently represents an alkyl group having 1 to 6 carbon atoms, a cycloalkyl group having 3 to 6 carbon atoms, or an aryl group having 6 to 12 carbon atoms, and $R^4$ and $R^5$ may be bonded to each other to form a ring. Above all, $R^4$ and $R^5$ are each preferably an alkyl group having 1 to 6 carbon atoms, and more preferably an alkyl group having 1 to 2 carbon atoms.

A part of hydrogen atoms of $R^4$ to $R^5$ may be substituted with a halogen atom.

Suitable examples of the alkyl group and the alkyl group in which a part of hydrogen atoms is substituted with a halogen atom, which are represented by $R^4$ and $R^5$, include a straight-chain alkyl group, such as a methyl group, an ethyl group, an n-propyl group, an n-butyl group, an n-pentyl group, an n-hexyl group, etc., a branched alkyl group, such as an isopropyl group, a sec-butyl group, a tert-butyl group, a tert-amyl group, etc., a fluoromethyl group, a trifluoromethyl group, a 2,2,2-trifluoroethyl group, and the like, with a methyl group, an ethyl group, an n-propyl group, or an n-butyl group being more preferred.

Suitable examples of the cycloalkyl group which is represented by $R^4$ and $R^5$ include a cycloalkyl group, such as a cyclopropyl group, a cyclobutyl group, a cyclopentyl group, a cyclohexyl group, etc.

Suitable examples of the aryl group and the aryl group in which a part of hydrogen atoms is substituted with a halogen atom, which are represented by $R^4$ and $R^5$, include a phenyl group, a 2-methylphenyl group, a 3-methylphenyl group, a 4-methylphenyl group, a 4-tert-butylphenyl group, a 2,4,6-trimethylphenyl group, a 2-fluorophenyl group, a 3-fluorophenyl group, a 4-fluorophenyl group, a 2,4-difluorophenyl group, a 2,6-difluorophenyl group, a 3,4-difluorophenyl group, a 2,4,6-trifluorophenyl group, a pentafluorophenyl group, a 4-trifluoromethylphenyl group, and the like, with a phenyl group being more preferred.

Suitable examples of the group when $R^4$ and $R^5$ are bonded to each other to form a ring include an ethane-1,2-diyl group, a propane-1,3-diyl group, a propane-1,2-diyl group, a butane-2,3-diyl group, and the like, with an ethane-1,2-diyl group being more preferred.

In the general formula (II), when m is 1, then $R^6$ represents an aryl group having 6 to 12 carbon atoms and is preferably an aryl group having 6 to 10 carbon atoms, and more preferably an aryl group having 6 to 8 carbon atoms.

When m is 1, as specific examples of $R^6$, there is suitably exemplified an aryl group, such as a phenyl group, a 2-methylphenyl group, a 3-methylphenyl group, a 4-methylphenyl group, a 4-tert-butylphenyl group, a 2-phenylphenyl group, a 4-phenylphenyl group, a 2-fluorophenyl group, a 4-fluorophenyl group, a 4-trifluoromethylphenyl group, a 2,4-difluorophenyl group, a perfluorophenyl group, etc.

Among the foregoing $R^6$, a phenyl group, a 4-methylphenyl group, a 4-tert-butylphenyl group, a 4-fluorophenyl group, a 4-trifluoromethylphenyl group, a 2-phenylphenyl group, a 4-phenylphenyl group, or a perfluorophenyl group is preferred, and a phenyl group, a 4-fluorophenyl group, a 4-trifluoromethylphenyl group, or a 2-phenylphenyl group is more preferred.

In the general formula (II), when m is 2, then $R^6$ represents an alkylene group having 2 to 6 carbon atoms, an alkenylene group having 4 to 8 carbon atoms, or an alkynylene group having 4 to 8 carbon atoms and is preferably an alkylene group having 2 to 5 carbon atoms, an alkenylene group having 4 to 6 carbon atoms, or an alkynylene group having 4 to 6 carbon atoms, and more preferably an alkylene group having 2 to 3 carbon atoms, an alkenylene group having 4 carbon atoms, or an alkynylene group having 4 carbon atoms.

When m is 2, suitable examples of $R^6$ include an alkylene group, such as an ethane-1,2-diyl group, a propane-1,3-diyl group, a propane-1,2-diyl group, a butane-1,4-diyl group, a butane-2,3-diyl group, etc., an alkenylene group, such as a 2-butene-1,4-diyl group, and an alkynylene group, such as a 2-butyne-1,4-diyl group, a 3-hexyne-2,5-diyl group, a 2,5-dimethyl-3-hexyne-2,5-diyl group, etc. Above all, an ethane-1,2-diyl group, a propane-1,2-diyl group, a butane-1,4-diyl group, a butane-2,3,-diyl group, a 2-butene-1,4-diyl group, a 2-butyne-1,4-diyl group, a 3-hexyne-2,5-diyl group, or a 2,5-dimethyl-3-hexyne-2,5-diyl group is preferred, and a 2-butene-1,4-diyl group or a 2-butyne-1,4-diyl group is more preferred.

As specific examples of the phosphonoformic acid compound represented by the general formula (II), there are suitably exemplified the following compounds.

[In the case of m=1: Phosphonoformic acid compound having a carbon-carbon unsaturated bond]

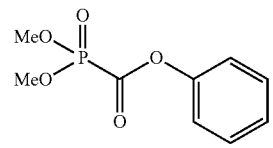

C1

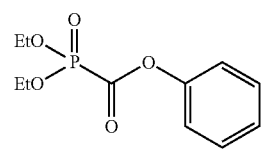

C2

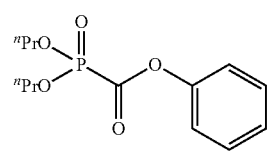

C3

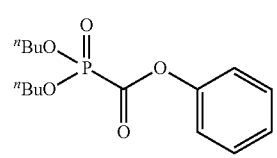

C4

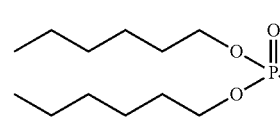

C5

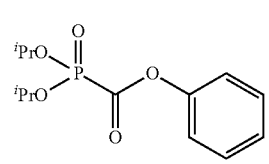

C6

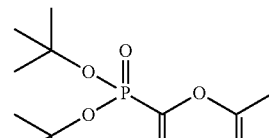

C7

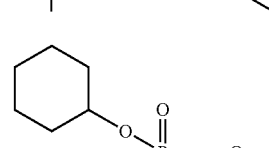

C8

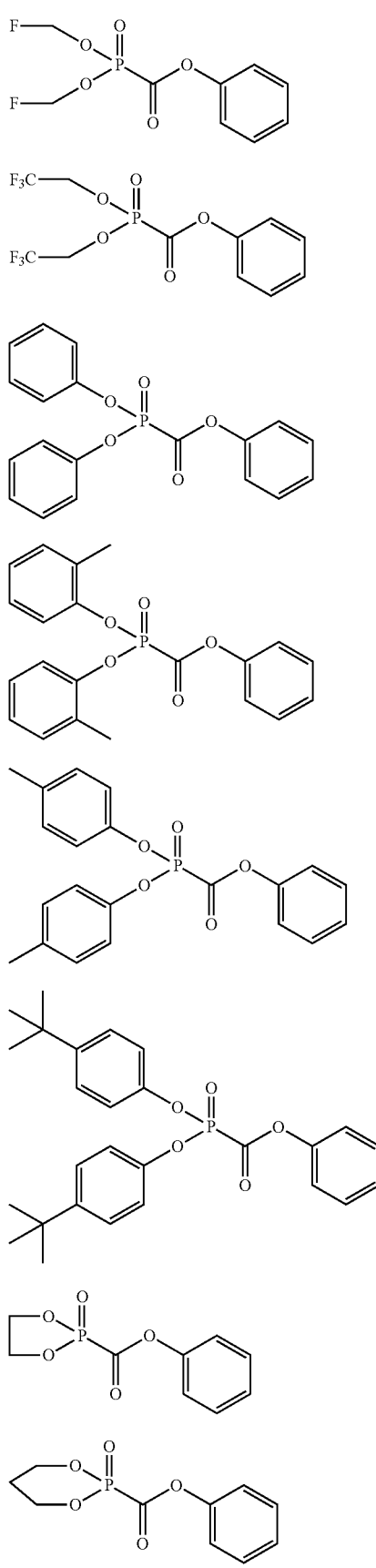
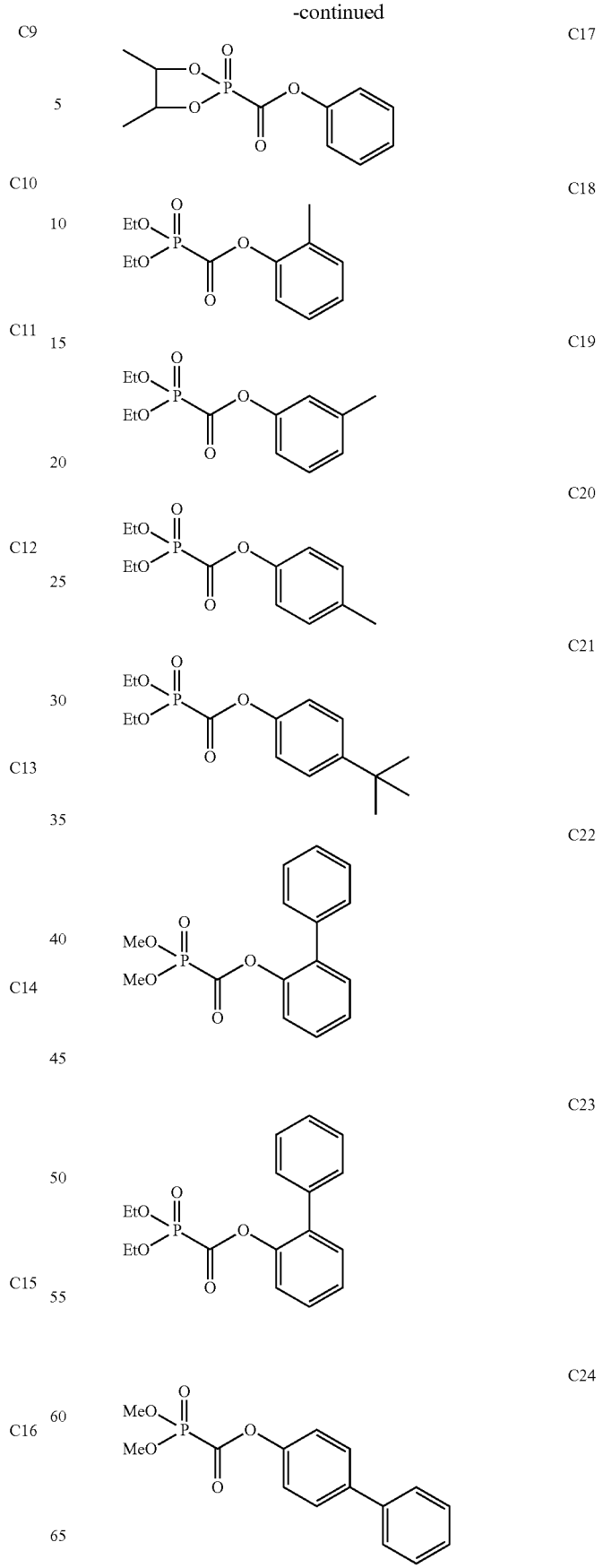

-continued

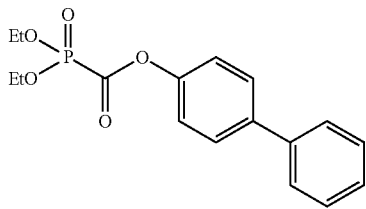
C25

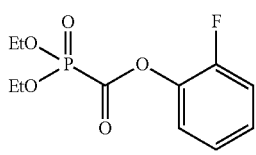
C26

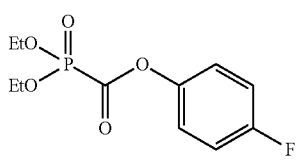
C27

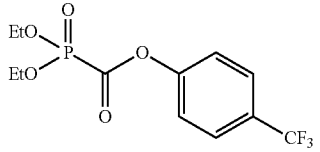
C28

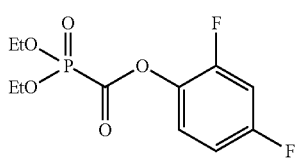
C29

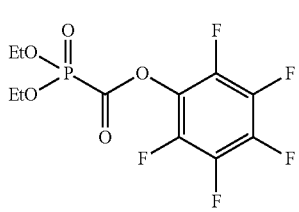
C30

[In the case of m=2: Phosphonoformic acid compound having two phosphonocarbonyl groups]

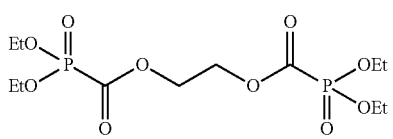
D1

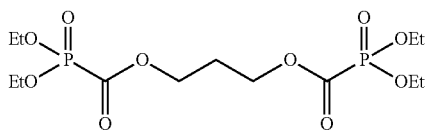
D2

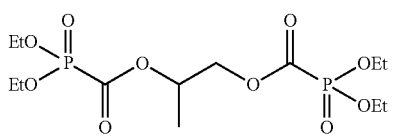
D3

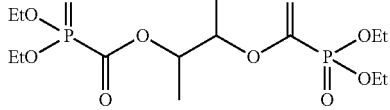
D4

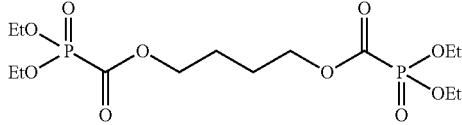
D5

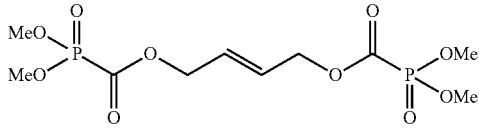
D6

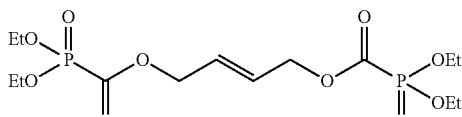
D7

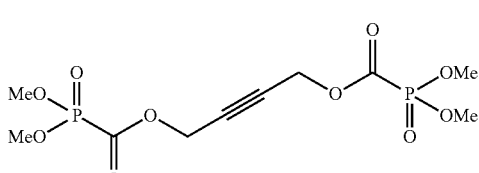
D8

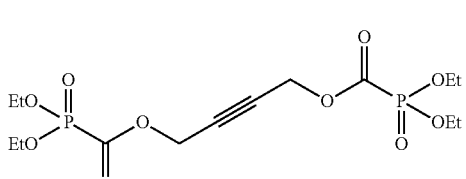
D9

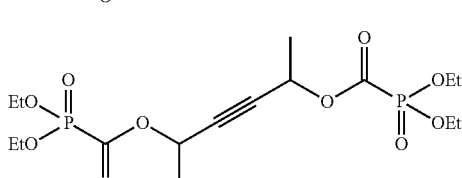
D10

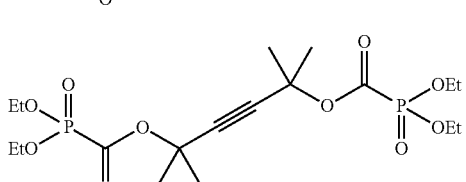
D11

Among the aforementioned compounds, Compounds C1 to C4, C10, C15, C18 to C30, D1, D3, D4, and D6 to D9 are preferred; one or more selected from phenyl (dimethoxyphosphoryl)formate (Compound C1), phenyl (diethoxyphosphoryl)formate (Compound C2), 2-phenylphenyl (dimethoxyphosphoryl)formate (Compound C22), 2-phenylphenyl (diethoxyphosphoryl)formate (Compound C23), 4-phenylphenyl (dimethoxyphosphoryl)formate (Compound C24), 4-phenylphenyl (diethoxyphosphoryl)formate (Compound C25), 4-fluorophenyl (diethoxyphosphoryl)formate (Compound C27), 4-trifluoromethylphenyl (diethoxyphosphoryl)formate (Compound C28), ethane-1,2-diyl bis((diethoxyphosphoryl)formate) (Compound D1), 2-butene-1,4-diyl bis((dimethoxyphosphoryl)formate) (Compound D6), 2-butene-1,4-diyl bis((diethoxyphosphoryl)formate) (Compound D7), 2-butyne-1,4-diyl bis((dimethoxyphosphoryl)formate) (Compound D8), 2-butyne-1,4-diyl bis((diethoxyphosphoryl)formate) (Compound D9), 3-hexyne-2,5-diyl bis((diethoxyphosphoryl)formate) (Compound D10), and 2,5-dimethyl-3-hexyne-2,5-diyl bis((diethoxyphosphoryl)formate) (compound D11) are more preferred; and one or more selected from phenyl (dimethoxyphosphoryl)formate (Compound C1), phenyl (diethoxyphosphoryl)formate (Compound C2), 2-phenylphenyl (dimethoxyphosphoryl)formate (Compound C22), 2-phenylphenyl (diethoxyphosphoryl)formate (Compound C23), 4-fluorophenyl (diethoxyphosphoryl)formate (Compound C27), 4-trifluoromethylphenyl (diethoxyphosphoryl)formate (Compound C28), 2-butene-1,4-diyl bis((dimethoxyphosphoryl)formate) (Compound D6), 2-butene-1,4-diyl bis((diethoxyphosphoryl)formate) (Compound D7), 2-butyne-1,4-diyl bis((dimethoxyphosphoryl)formate) (Compound D8), and 2-butyne-1,4-diyl bis((diethoxyphosphoryl)formate) (Compound D9) are still more preferred.

When the phosphonoformic acid compound falling within the aforementioned scope is contained in the nonaqueous electrolytic solution, it is possible to greatly improve the high-load charging and discharging cycle properties of the energy storage device at a high temperature and to suppress worsening of the heat stability of a negative electrode, and hence, such is preferred.

In the nonaqueous electrolytic solution of the present invention, a content of the phosphonoformic acid compound represented by the foregoing general formula (I), which is contained in the nonaqueous electrolytic solution, is preferably 0.001 to 5% by mass in the nonaqueous electrolytic solution. When the content is 5% by mass or less, there is less concern that a surface film is excessively formed on the electrode, thereby worsening the high-temperature cycle properties, whereas when it is 0.001% by mass or more, the formation of a surface film is sufficient, and an improving effect of the high-temperature cycle properties is enhanced. The content is preferably 0.05% by mass or more, and more preferably 0.2% by mass or more in the nonaqueous electrolytic solution. An upper limit thereof is preferably 4% by mass or less, more preferably 2.5% by mass or less, and especially preferably 1.5% by mass or less.

In the nonaqueous electrolytic solution of the present invention, by combining at least one selected from the phosphonoformic acid compound having at least one carbon-carbon unsaturated bond, which is represented by the foregoing general formula (I), and the phosphonoformic acid compound having a carbon-carbon unsaturated bond or two phosphonocarbonyl groups, which is represented by the general formula (II), with a nonaqueous solvent, an electrolyte salt, and further other additives as described below, a peculiar effect that electrochemical characteristics, such as the high-load charging and discharging cycle properties at a high temperature, the heat stability of a negative electrode, etc., are synergistically improved is revealed.

[Nonaqueous Solvent]

As the nonaqueous solvent which is used for the nonaqueous electrolytic solution of the present invention, there are suitably exemplified a cyclic carbonate, a linear ester, a lactone, an ether, and an amide, and it is more preferred that both a cyclic carbonate and a linear ester are included.

The term "linear ester" is used as a concept including a linear carbonate and a linear carboxylic acid ester.

<Cyclic Carbonate>

Examples of the cyclic carbonate include one or more selected from ethylene carbonate (EC), propylene carbonate (PC), 1,2-butylene carbonate, 2,3-butylene carbonate, a cyclic carbonate having a fluorine atom or an unsaturated bond, and the like.

As the cyclic carbonate having a fluorine atom, one or more selected from 4-fluoro-1,3-dioxolan-2-one (FEC) and trans- or cis-4,5-difluoro-1,3-dioxolan-2-one (the both will be hereunder named generically as "DFEC") are preferred.

Examples of the cyclic carbonate having an unsaturated bond include a cyclic carbonate having an unsaturated bond, such as a carbon-carbon double bond, a carbon-carbon triple bond, etc.

Examples of the cyclic carbonate having an unsaturated bond include one or more selected from vinylene carbonate (VC), vinyl ethylene carbonate (VEC), 4-ethynyl-1,3-dioxolan-2-one (EEC), and the like. One or more selected from vinylene carbonate (VC), vinyl ethylene carbonate (VEC), and 4-ethynyl-1,3-dioxolan-2-one (EEC) are preferred.

Use of at least one of the aforementioned cyclic carbonates having a fluorine atom or an unsaturated bond is preferred because in the case of using the energy storage device under a high voltage, the gas generation after the cycle may be much more suppressed, and it is more preferred to contain both the aforementioned cyclic carbonate having a fluorine atom and the aforementioned cyclic carbonate having an unsaturated bond.

When a content of the cyclic carbonate having an unsaturated bond is preferably 0.07% by volume or more, more preferably 0.2% by volume or more, and still more preferably 0.7% by volume or more relative to a total volume of the nonaqueous solvent, and an upper limit thereof is preferably 7% by volume or less, more preferably 4% by volume or less, and still more preferably 2.5% by volume or less, the stability of a surface film is increased, and in the case of using the energy storage device at a high temperature, the charging and discharging cycle properties are improved, and hence, such is preferred.

When a content of the cyclic carbonate having a fluorine atom is preferably 0.07% by volume or more, more preferably 4% by volume or more, and still more preferably 7% by volume or more relative to a total volume of the nonaqueous solvent, and an upper limit thereof is preferably 35% by volume or less, more preferably 25% by volume or less, and still more preferably 15% by volume or less, the stability of a surface film is increased, and in the case of using the energy storage device under a high voltage, the charging and discharging cycle properties are improved, and hence, such is preferred.

In the case where the nonaqueous solvent includes both the aforementioned cyclic carbonate having an unsaturated bond and the aforementioned cyclic carbonate having a fluorine atom, when a proportion of the content of the cyclic carbonate having an unsaturated bond to the content of the cyclic carbonate having a fluorine atom is preferably 0.2% or more, more preferably 3% or more, and still more preferably 7% or more, and an upper limit thereof is preferably 40% or less, more preferably 30% or less, and still more preferably 15% or less, the stability of a surface film is increased, and in the case of using the energy storage device at a high temperature, the charging and discharging cycle properties are improved, and hence, such is especially preferred.

When the nonaqueous solvent includes one or more selected from ethylene carbonate and propylene carbonate, the resistance of a surface film formed on the electrode becomes small, and hence, such is preferred. A content of one or more selected from ethylene carbonate and propylene carbonate is preferably 3% by volume or more, more preferably 5% by volume or more, and still more preferably 7% by volume or more relative to a total volume of the nonaqueous solvent, and an upper limit thereof is preferably 45% by volume or less, more preferably 35% by volume or less, and still more preferably 25% by volume or less.

In the case where the nonaqueous solvent includes both ethylene carbonate and propylene carbonate, when a proportion of the content of propylene carbonate to the content of ethylene carbonate is preferably 10% or more, more preferably 20% or more, and still more preferably 25% or more, and an upper limit thereof is preferably 90% or less, more preferably 80% or less, still more preferably 50% or less, and especially preferably 40% or less, the resistance of a surface film becomes smaller, and even in the case of using the energy storage device at a high load, there is less concern that lithium is electrodeposited, and hence, such is preferred.

These solvents may be used solely; in the case where a combination of two or more of the solvents is used, the electrochemical characteristics at a high temperature are more improved, and hence, such is preferred; and use of a combination of three or more thereof is especially preferred. As suitable combinations of these cyclic carbonates, EC and PC; EC and VC; PC and VC; VC and FEC; EC and FEC; PC and FEC; FEC and DFEC; EC and DFEC; PC and DFEC; VC and DFEC; VEC and DFEC; VC and EEC; EC and EEC; EC, PC and VC; EC, PC and FEC; EC, VC and FEC; EC, VC and VEC; EC, VC and EEC; EC, EEC and FEC; PC, VC and FEC; EC, VC and DFEC; PC, VC and DFEC; EC, PC, VC and FEC; EC, PC, VC and DFEC; and the like are preferred. Among the aforementioned combinations, a combination, such as EC and VC; EC and FEC; PC and FEC; EC, PC and VC; EC, PC and FEC; EC, VC and FEC; EC, VC and EEC; EC, EEC and FEC; PC, VC and FEC; EC, PC, VC and FEC; etc., is more preferred. A combination of EC, PC and VC; EC, PC and FEC; PC, VC and FEC; or EC, PC, VC and FEC is still more preferred.

<Linear Ester>

As the linear ester, there are suitably exemplified one or more asymmetric linear carbonates selected from methyl ethyl carbonate (MEC), methyl propyl carbonate (MPC), methyl isopropyl carbonate (MIPC), methyl butyl carbonate, ethyl propyl carbonate, and the like; one or more symmetric linear carbonates selected from dimethyl carbonate (DMC), diethyl carbonate (DEC), dipropyl carbonate, dibutyl carbonate, and the like; and one or more linear carboxylic acid esters selected from a pivalic acid ester, such as methyl pivalate, ethyl pivalate, propyl pivalate, etc., methyl propionate, ethyl propionate, methyl acetate, ethyl acetate, and the like.

Among the aforementioned linear esters, a linear ester having a methyl group, which is selected from dimethyl carbonate, methyl ethyl carbonate, methyl propyl carbonate, methyl isopropyl carbonate, methyl butyl carbonate, methyl propionate, methyl acetate, and ethyl acetate, is preferred, and a linear carbonate having a methyl group is especially preferred.

In the case of using a linear carbonate, it is preferred to use two or more thereof. Furthermore, it is more preferred that both the symmetric linear carbonate and the asymmetric linear carbonate are included, and it is still more preferred that a content of the symmetric linear carbonate is more than a content of the asymmetric linear carbonate.

Although a content of the linear ester is not particularly limited, it is preferred to use the linear ester in an amount in the range of from 60 to 90% by volume relative to a total volume of the nonaqueous solvent. When the content is 60% by volume or more, the viscosity of the nonaqueous electrolytic solution does not become excessively high, and when it is 90% by volume or less, there is less concern that an electroconductivity of the nonaqueous electrolytic solution is decreased, whereby the electrochemical characteristics at a high temperature are worsened, and therefore, it is preferred that the content of the linear ester falls within the aforementioned range.

A proportion of the volume occupied by the symmetric linear carbonate in the linear carbonate is preferably 51% by volume or more, and more preferably 55% by volume or more. An upper limit thereof is preferably 95% by volume or less, and more preferably 85% by volume or less. It is especially preferred that diethyl carbonate is included in the symmetric linear carbonate. It is more preferred that the asymmetric linear carbonate has a methyl group, and methyl ethyl carbonate is especially preferred.

The aforementioned case is preferred because the electrochemical characteristics at a high temperature are much more improved.

As for a proportion of the cyclic carbonate and the linear ester, from the viewpoint of improving the electrochemical characteristics at a high temperature, a ratio of the cyclic carbonate to the linear ester (volume ratio) is preferably 10/90 to 45/55, more preferably 15/85 to 40/60, and especially preferably 20/80 to 35/65.

<Other Nonaqueous Solvents>

As other nonaqueous solvents, there are suitably exemplified one or more selected from a cyclic ether, such as tetrahydrofuran, 2-methyltetrahydrofuran, 1,3-dioxolane, 1,3-dioxane, 1,4-dioxane, etc.; a linear ether, such as 1,2-dimethoxyethane, 1,2-diethoxyethane, 1,2-dibutoxyethane, etc.; an amide, such as dimethylformamide, etc.; a sulfone, such as sulfolane, etc.; and a lactone, such as γ-butyrolactone, γ-valerolactone, α-angelicalactone, etc.

<Other Additives>

For the purpose of much more improving the heat stability of a negative electrode, it is preferred to further add other additives in the nonaqueous electrolytic solution. Examples of other additives include one or more selected from (a) an S(=O) group-containing compound, (b) a fluorinated benzene compound, (c) a carbon-carbon triple bond-containing compound, (d) a carboxylic acid anhydride, (e) a cyclic acetal compound, (f) an isocyanate compound, (g) a nitrile compound, (h) a benzene compound, (i) a phosphazene compound, and the like.

As (a) the S(=O) group-containing compound, its kind is not particularly limited so long as it is a compound having an "S(=O) group" in a molecule thereof.

As the S(=O) group-containing compound, specifically, there are suitably exemplified one or more S(=O) group-containing compounds selected from a sultone, such as 1,3-propanesultone, 1,3-butanesultone, 2,4-butanesultone, 1,4-butanesultone, 1,3-propanesultone, 2,2-dioxide-1,2-oxathiolane-4-yl acetate, 5,5-dimethyl-1,2-oxathiolane-4-one 2,2-dioxide, etc., ethylene sulfite, butane-2,3-diyl dimethanesulfonate, butane-1,4-diyl dimethanesulfonate, pentane-1,5-diyl dimethanesulfonate, methylene methanedisulfonate, divinylsulfone, and the like.

Among those, one or more selected from 1,3-propanesultone, 1,4-butanesultone, 2,4-butanesultone, 2,2-dioxide-1,2-oxathiolane-4-yl acetate, 5,5-dimethyl-1,2-oxathiolane-4-one 2,2-dioxide, butane-2,3-diyl dimethanesulfonate, and divinylsulfone are more preferred.

As (b) the fluorinated benzene compound, its kind is not particularly limited so long as it is a compound having a "phenyl group in which at least a part of the benzene ring is substituted with fluorine" in a molecule thereof.

As the fluorinated benzene compound, specifically, there are suitably exemplified one or more fluorinated benzene compounds selected from fluorobenzene, difluorobenzene (including o-, m-, and p-forms), 2,4-difluoroanisole, 1-fluoro-2-cyclohexylbenzene, 1-fluoro-3-cyclohexylbenzene, 1-fluoro-4-cyclohexylbenzene, pentafluorophenyl methanesulfonate, 2-fluorophenyl methanesulfonate, 3-fluorophenyl methanesulfonate, 4-fluorophenyl methanesulfonate, 2,4-difluorophenyl methanesulfonate, 3,4-difluorophenyl methanesulfonate, 2,3,4-trifluorophenyl methanesulfonate, 2,3,5,6-tetrafluorophenyl methanesulfonate, 4-fluoro-3-trifluoromethylphenyl methanesulfonate, and 4-fluoro-3-trifluoromethylphenyl methyl carbonate.

Among those, one or more selected from fluorobenzene, 2,4-difluoroanisole, 1-fluoro-4-cyclohexylbenzene, pentafluorophenyl methanesulfonate, 2-fluorophenyl methanesulfonate, 2,4-difluorophenyl methanesulfonate, and 4-fluoro-3-trifluoromethylphenyl methanesulfonate are more preferred.

As (c) the carbon-carbon triple bond-containing compound, its kind is not particularly limited so long as it is a compound having a "carbon-carbon triple bond" in a molecule thereof.

As the carbon-carbon triple bond-containing compound, specifically, there are suitably exemplified 2-propynyl methyl carbonate, 2-propynyl acetate, 2-propynyl formate, 2-propynyl methacrylate, 2-propynyl methanesulfonate, 2-propynyl vinylsulfonate, 2-propynyl 2-(methanesulfonyloxy)propionate, di(2-propynyl) oxalate, methyl 2-propynyl oxalate, ethyl 2-propynyl oxalate, di(2-propynyl) glutarate, 2-butyne-1,4-diyl dimethanesulfonate, 2-butyne-1,4-diyl diformate, 2,4-hexadiyne-1,6-diyl dimethanesulfonate, and the like.

Among those, one or more selected from 2-propynyl methyl carbonate, 2-propynyl methacrylate, 2-propynyl methanesulfonate, 2-propynyl vinylsulfonate, 2-propynyl 2-(methanesulfonyloxy)propionate, di(2-propynyl) oxalate, methyl 2-propynyl oxalate, ethyl 2-propynyl oxalate, and 2-butyne-1,4-diyl dimethanesulfonate are more preferred.

As (d) the carboxylic acid anhydride, its kind is not particularly limited so long as it is a compound having a "C(=O)—O—C(=O) group" in a molecule thereof.

As the carboxylic acid anhydride, specifically, there are suitably exemplified a linear carboxylic acid anhydride, such as acetic anhydride, propionic anhydride, etc., a cyclic acid anhydride, such as succinic anhydride, maleic anhydride, allyl succinic anhydride, glutaric anhydride, itaconic anhydride, 3-sulfo-propionic anhydride, etc., and the like.

Among those, one or more selected from succinic anhydride, maleic anhydride, and allyl succinic anhydride are more preferred.

As (e) the cyclic acetal compound, its kind is not particularly limited so long as it is a compound having an "acetal group" in a molecule thereof.

As the cyclic acetal compound, specifically, there are suitably exemplified 1,3-dioxolane, 1,3-dioxane, 1,3,5-trioxane, and the like.

Among those, 1,3-dioxolane or 1,3-dioxane is more preferred, and 1,3-dioxane is still more preferred.

As (f) the isocyanate compound, its kind is not particularly limited so long as it is a compound having an "N=C=O group" in a molecule thereof.

As the isocyanate compound, specifically, there are suitably exemplified methyl isocyanate, ethyl isocyanate, butyl isocyanate, phenyl isocyanate, tetramethylene diisocyanate, hexamethylene diisocyanate, octamethylene diisocyanate, 1,4-phenylene diisocyanate, 2-isocyanatoethyl acrylate, 2-isocyanatoethyl methacrylate, and the like.

Among those, one or more selected from hexamethylene diisocyanate, octamethylene diisocyanate, 2-isocyanatoethyl acrylate, and 2-isocyanatoethyl methacrylate are more preferred, and one or more selected from hexamethylene diisocyanate, 2-isocyanatoethyl acrylate, and 2-isocyanatoethyl methacrylate are still more preferred.

As (g) the nitrile compound, its kind is not particularly limited so long as it is a compound having a "nitrile group" in a molecule thereof.

As the nitrile compound, specifically, there are suitably exemplified acetonitrile, propionitrile, succinonitrile, glutaronitrile, adiponitrile, pimelonitrile, suberonitrile, sebaconitrile, and the like.

Among those, one or more selected from succinonitrile, glutaronitrile, adiponitrile, pimelonitrile, and sebaconitrile are more preferred, and one or more selected from succinonitrile, glutaronitrile, adiponitrile, and pimelonitrile are still more preferred.

As (h) the benzene compound, its kind is not particularly limited so long as it is a compound having a "phenyl group" in a molecule thereof.

As the benzene compound, specifically, there are suitably exemplified an aromatic compound having a branched alkyl group, such as cyclohexylbenzene, tert-butylbenzene, tert-amylbenzene, etc., biphenyl, terphenyl (including o-, m-, and p-forms), diphenyl ether, anisole, a partial hydride of terphenyl (e.g., 1,2-dicyclohexylbenzene, 2-phenylbicyclohexyl, 1,2-diphenylcyclohexane, and o-cyclohexylbiphenyl), a phenyl carbonate compound, such as methyl phenyl carbonate, ethyl phenyl carbonate, diphenyl carbonate, etc., and the like.

Among those, one or more selected from cyclohexylbenzene, tert-butylbenzene, tert-amylbenzene, biphenyl, terphenyl (including o-, m-, and p-forms), methyl phenyl carbonate, ethyl phenyl carbonate, and diphenyl carbonate are more preferred.

As (i) the phosphazene compound, its kind is not particularly limited so long as it is a compound having an "N=P—N group" in a molecule thereof.

As the phosphazene compound, specifically, there are suitably exemplified methoxypentafluorocyclotriphosphazene, ethoxypentafluorocyclotriphosphazene, phenoxypentafluorocyclotriphosphazene, ethoxyheptafluorocyclotetraphosphazene, and the like.

Among those, one or more cyclic phosphazene compounds selected from methoxypentafluorocyclotriphosphazene, ethoxypentafluorocyclotriphosphazene, phenoxypentafluorocyclotriphosphazene, and the like are more preferred.

Of the foregoing, it is preferred to include at least one selected from (e) the cyclic acetal compound, (f) the isocyanate compound, (g) the nitrile compound, and (h) the benzene compound, with two or more thereof being more preferred. In the cyclic acetal compound, 1,3-dioxane is still more preferred.

A content of (e) the cyclic acetal compound, (f) the isocyanate compound, (g) the nitrile compound, or (h) the benzene compound is preferably 0.001 to 5% by mass in the nonaqueous electrolytic solution. When the content of such a compound is 0.001% by mass or more, the formation of a surface film is sufficient, and an improving effect of the high-temperature cycle properties are enhanced. The content is more preferably 0.01% by mass or more, and still more preferably 0.1% by mass or more in the nonaqueous electrolytic solution. An upper limit thereof is more preferably 3.5% by mass or less, and still more preferably 2.5% by mass or less.

A ratio (mass ratio) of at least one selected from the phosphonoformic acid compound having at least one carbon-carbon unsaturated bond, which is represented by the general formula (I), and the phosphonoformic acid compound having a carbon-carbon unsaturated bond or two phosphonocarbonyl groups, which is represented by the general formula (II), according to the present invention to at least one selected from (e) the cyclic acetal compound, (f) the isocyanate compound, (g) the nitrile compound, and (h) the benzene compound is preferably 2/98 to 95/5, more preferably 10/90 to 85/15, and still more preferably 30/70 to 45/55. This is because when the ratio falls within the foregoing range, the heat stability of a negative electrode may be much more improved.

[Electrolyte Salt]

As the electrolyte salt which is used in the present invention, there are suitably exemplified the following first lithium salt and second lithium salt.

(First Lithium Salt)

As the first lithium salt, there are suitably exemplified an inorganic lithium salt, such as $LiPF_6$, $LiBF_4$, $LiClO_4$, etc.; a linear fluoroalkyl group-containing lithium salt, such as $LiN(SO_2F)_2$, $LiN(SO_2CF_3)_2$, $LiN(SO_2C_2F_5)_2$, $LiCF_3SO_3$, $LiC(SO_2CF_3)_3$, $LiPF_4(CF_3)_2$, $LiPF_3(C_2F_5)_3$, $LiPF_3(CF_3)_3$, $LiPF_3(iso-C_3F_7)_3$, $LiPF_5(iso-C_3F_7)$, etc.; and a cyclic fluoroalkylene chain-containing lithium salt, such as $(CF_2)_2(SO_2)_2NLi$, $(CF_2)_3(SO_2)_2NLi$, etc. One or more thereof may be used solely or in admixture.

Among those, one or more selected from $LiPF_6$, $LiBF_4$, $LiN(SO_2CF_3)_2$, $LiN(SO_2C_2F_5)_2$, and $LiN(SO_2F)_2$ are more preferred; one or more selected from $LiPF_6$, $LiBF_4$, $LiN(SO_2CF_3)_2$, and $LiN(SO_2F)_2$ are more preferred; and it is most preferred to use $LiPF_6$.

In general, a concentration of the first lithium salt is generally 0.3 M or more, more preferably 0.7 M or more, and still more preferably 1.1 M or more relative to the aforementioned nonaqueous solvent. An upper limit thereof is preferably 2.5 M or less, more preferably 2.0 M or less, and still more preferably 1.6 M or less.

In order to improve the permeability of a lithium ion without worsening the heat stability of a negative electrode, it is preferred to use a second lithium salt in combination with the first lithium salt.

(Second Lithium Salt)

Use of a combination with, as the second lithium salt, one or more selected from an $S(=O)_2O$ structure-containing lithium salt, a $P=O$ or $Cl=O$ structure-containing lithium salt, and a lithium salt having an oxalate complex as an anion is preferred.

As the $S(=O)_2O$ structure-containing lithium salt, there are suitably exemplified one or more selected from lithium fluorosulfonate ($LiSO_3F$), $LiCF_3SO_3$, $CH_3SO_4Li$, lithium ethyl sulfate ($C_2H_5SO_4Li$), and $C_3H_7SO_4Li$.

As the $P=O$ structure-containing lithium salt, there are suitably exemplified one or more selected from $LiPO_2F_2$ and $Li_2PO_3F$.

As the lithium salt having an oxalate complex as an anion, there are suitably exemplified one or more selected from a lithium salt having a boron-containing oxalate complex as an anion, such as lithium bis[oxalate-O,O']borate (LiBOB), lithium difluoro[oxalate-O,O']borate (LiDFOB), etc., and a lithium salt having a phosphorus-containing oxalate as an anion, such as lithium difluorobis[oxalate-O,O']phosphate (LiDFOP), lithium tetrafluoro[oxalate-O,O']phosphate (LiTFOP), etc.

Of the foregoing second lithium salts, an $S(=O)_2O$ structure-containing lithium salt, a $P=O$ structure-containing lithium salt, or a lithium salt having a boron-containing oxalate complex as an anion is more preferred.

A total content of the second lithium salt is preferably 0.001 to 10% by mass in the nonaqueous electrolytic solution. When the content is 10% by mass or less, there is less concern that a surface film is excessively formed on a negative electrode, thereby worsening the permeability of a lithium ion, whereas when it is 0.001% by mass or more, the formation of a surface film is sufficient, and an improving effect of the heat stability is enhanced. The content is preferably 0.05% by mass or more, more preferably 0.1% by mass or more, and still more preferably 0.2% by mass or more in the nonaqueous electrolytic solution. An upper limit thereof is preferably 5% by mass or less, more preferably 3% by mass or less, and still more preferably 2% by mass or less.

A mass ratio of at least one selected from the phosphonoformic acid compound having at least one carbon-carbon unsaturated bond, which is represented by the general formula (I), and the phosphonoformic acid compound having a carbon-carbon unsaturated bond or two phosphonocarbonyl groups, which is represented by the general formula (II), according to the present invention to the second lithium salt is preferably 10/90 to 98/2, more preferably 30/70 to 95/5, and still more preferably 60/40 to 87/13. When the ratio falls within the foregoing range, the permeability of a lithium ion can be more improved without worsening the heat stability of a negative electrode, and hence, such is preferred.

As a suitable combination of the first lithium salt with the second lithium salt, it is especially preferred that the nonaqueous electrolytic solution includes $LiPF_6$ as the first lithium salt and at least one selected from $LiSO_3F$, $CH_3SO_4Li$, $C_2H_5SO_4Li$, $LiPO_2F_2$, LiBOB, and LiDFOB as the second lithium salt.

[Production of Nonaqueous Electrolytic Solution]

The nonaqueous electrolytic solution of the present invention may be obtained, for example, by mixing the aforementioned nonaqueous solvent, adding the aforementioned electrolyte salt thereto, and further adding 0.001 to 5% by mass of at least one selected from the phosphonoformic acid compound represented by the foregoing general formula (I) and the phosphonoformic acid compound represented by the foregoing general formula (II) to the resulting nonaqueous electrolytic solution.

At this time, the nonaqueous solvent to be used and the compounds to be added to the nonaqueous electrolytic solution are preferably purified in advance to decrease impurities as far as possible within the range where the productivity is not remarkably worsened.

The nonaqueous electrolytic solution of the present invention may be used in first to fourth energy storage devices shown below, in which the nonaqueous electrolytic solution may be used as the nonaqueous electrolyte not only in the form of a liquid but also in the form of gel. Furthermore, the nonaqueous electrolytic solution of the present invention may also be used for a solid polymer electrolyte. Above all, the nonaqueous electrolytic solution is preferably used in the first energy storage device using a lithium salt as the electrolyte salt (namely, for a lithium battery) or in the fourth energy storage device (namely, for a lithium ion capacitor), more preferably used in a lithium battery, and most suitably used in a lithium secondary battery.

[First Energy Storage Device (Lithium Battery)]

The lithium battery as referred to in the present specification is a generic name for a lithium primary battery and a lithium secondary battery. In the present specification, the term "lithium secondary battery" is used as a concept also including a so-called lithium ion secondary battery. The lithium battery of the present invention includes a positive electrode, a negative electrode, and the aforementioned nonaqueous electrolytic solution having an electrolyte salt dissolved in a nonaqueous solvent. Other constitutional members than the nonaqueous electrolytic solution, such as the positive electrode, the negative electrode, etc., may be used without being particularly limited.

For example, examples of a positive electrode active material used for a lithium secondary battery include a complex metal oxide containing lithium and one or more selected from cobalt, manganese, and nickel. Such a positive electrode active material may be used solely or in combination of two or more thereof.

Examples of the lithium complex metal oxide include $LiCoO_2$, $LiMn_2O_4$, $LiNiO_2$, $LiCo_{1-x}Ni_xO_2$ (0.01<x<1), $LiCo_{1/3}Ni_{1/3}Mn_{1/3}O_2$, $LiNi_{1/2}Mn_{3/2}O_4$, $LiCo_{0.98}Mg_{0.02}O_2$, and the like. These materials may be used as a combination, such as a combination of $LiCoO_2$ and $LiMn_2O_4$, a combination of $LiCoO_2$ and $LiNiO_2$, and a combination of $LiMn_2O_4$ and $LiNiO_2$.

For improving the safety on overcharging and the cycle properties, and for enabling the use at a charge potential of 4.3 V or more, a part of the lithium complex metal oxide may be substituted with other elements. For example, a part of cobalt, manganese, or nickel may be substituted with at least one element selected from Sn, Mg, Fe, Ti, Al, Zr, Cr, V, Ga, Zn, Cu, Bi, Mo, La, and the like, a part of O may be substituted with S or F, or the oxide may be coated with a compound containing any of such other elements.

Among those, a lithium complex metal oxide capable of being used at a charge potential of the positive electrode in a fully-charged state of 4.3 V or more based on Li, such as $LiCoO_2$, $LiMn_2O_4$, and $LiNiO_2$, is preferred; and a lithium complex metal oxide capable of being used at 4.4 V or more, such as $LiCo_{1-x}M_xO_2$ (wherein M represents one or more elements selected from Sn, Mg, Fe, Ti, Al, Zr, Cr, V, Ga, Zn, and Cu, and 0.001≤x≤0.05), $LiNi_{1/3}Mn_{1/3}Co_{1/3}O_2$, $LiNi_{1/2}Mn_{3/2}O_4$, and a solid solution of $Li_2MnO_3$ and $LiMO_2$ (wherein M represents a transition metal, such as Co, Ni, Mn, Fe, etc.), is more preferred. The use of the lithium complex metal oxide capable of acting at a high charge voltage is liable to worsen the electrochemical characteristics particularly at a high temperature due to the reaction with the electrolytic solution on charging, but in the lithium secondary battery according to the present invention, worsening of the electrochemical characteristics can be suppressed. In particular, a battery with a positive electrode containing Mn tends to have an increased resistance of the battery due to elution of an Mn ion from the positive electrode, thereby providing the tendency of worsening the electrochemical characteristics in the case of using it in a broad temperature range. However, the lithium secondary battery according to the present invention is preferred because worsening of the electrochemical characteristics can be suppressed.

In the case where when 10 g of the aforementioned positive electrode active material is dispersed in 100 mL of distilled water, a pH of a supernatant thereof is 10.0 to 12.5, the high-temperature cycle properties are apt to be much more obtained, and hence, such is preferred. The case where the pH is 10.5 to 12.0 is more preferred.

In the case where Ni is included as an element in the positive electrode, the content of impurities, such as LiOH, etc., in the positive electrode active material tends to increase, and the high-temperature cycle properties are apt to be much more obtained, and hence, such is preferred. The case where an atomic concentration of Ni in the positive electrode active material is 5 to 25 atomic % is more preferred, and the case where the atomic concentration of Ni is 8 to 21 atomic % is especially preferred.

Furthermore, a lithium-containing olivine-type phosphate may also be used as the positive electrode active material. In particular, a lithium-containing olivine-type phosphate including one or more selected from iron, cobalt, nickel, and manganese is preferred. As specific examples thereof, there are exemplified one or more selected from $LiFePO_4$, $LiCoPO_4$, $LiNiPO_4$, $LiMnPO_4$, and $LiFe_{1-x}Mn_xPO_4$ (0.1<x<0.9). Among those, $LiFePO_4$ or $LiMnPO_4$ is more preferred, and $LiFePO_4$ is still more preferred.

A part of such a lithium-containing olivine-type phosphate may be substituted with other element. A part of iron, cobalt, nickel, or manganese may be substituted with one or more elements selected from Co, Mn, Ni, Mg, Al, B, Ti, Nb, Cu, Zn, Mo, Ca, Sr, W, Zr, and the like, or the phosphate may be coated with a compound containing any of these other elements or with a carbon material. Among those, $LiFePO_4$ or $LiMnPO_4$ is preferred.

The lithium-containing olivine-type phosphate may also be used, for example, in admixture with the aforementioned positive electrode active material.

Since the lithium-containing olivine-type phosphate forms a stable phosphate skeleton ($PO_4$) structure and is excellent in heat stability on charging, it is possible to suppress worsening of the heat stability of a negative electrode and to further improve the safety of an energy storage device while maintaining the high-load charging and discharging cycle properties at a high temperature.

Examples of the positive electrode for a lithium primary battery include an oxide or chalcogen compound of one or more metal elements, such as $CuO$, $Cu_2O$, $Ag_2O$, $Ag_2CrO_4$, $CuS$, $CuSO_4$, $TiO_2$, $TiS_2$, $SiO_2$, $SnO$, $V_2O_5$, $V_6O_{12}$, $VO_x$, $Nb_2O_5$, $Bi_2O_3$, $Bi_2Pb_2O_5$, $Sb_2O_3$, $CrO_3$, $Cr_2O_3$, $MoO_3$, $WO_3$, $SeO_2$, $MnO_2$, $Mn_2O_3$, $Fe_2O_3$, $FeO$, $Fe_3O_4$, $Ni_2O_3$, $NiO$, $CoO_3$, $CoO$, and the like; a sulfur compound, such as $SO_2$, $SOCl_2$, etc.; a carbon fluoride (graphite fluoride) represented by a general formula $(CF_x)_n$; and the like. Among those, $MnO_2$, $V_2O_5$, graphite fluoride, and the like are preferred.

An electroconductive agent of the positive electrode is not particularly limited so long as it is an electron-conductive material that does not undergo chemical change. Examples thereof include graphites, such as natural graphite (e.g., flaky graphite, etc.), artificial graphite, etc., carbon blacks, such as acetylene black, Ketjen black, channel black, furnace black, lamp black, thermal black, etc., and the like. The graphite and the carbon black may be appropriately mixed and used. An amount of the electroconductive agent added to a positive electrode mixture is preferably 1 to 10% by mass, and especially preferably 2 to 5% by mass.

The positive electrode can be produced in such a manner that the positive electrode active material is mixed with an electroconductive agent, such as acetylene black, carbon black, etc., and then mixed with a binder, such as polytetrafluoroethylene (PTFE), polyvinylidene fluoride (PVDF), a copolymer of styrene and butadiene (SBR), a copolymer of acrylonitrile and butadiene (NBR), carboxymethyl cellulose (CMC), an ethylene-propylene-diene terpolymer, etc., to which is then added a high-boiling point solvent, such as 1-methyl-2-pyrrolidone, etc., followed by kneading to provide a positive electrode mixture, and the positive electrode mixture is applied onto a collector, such as an aluminum foil, a stainless steel-made lath plate, etc., dried, shaped under pressure, and then heat-treated in vacuum at a temperature of about 50° C. to 250° C. for about 2 hours.

A density of the positive electrode except for the collector is generally 1.5 g/cm$^3$ or more, and for the purpose of further increasing a capacity of the battery, the density is preferably 2 g/cm$^3$ or more, more preferably 3 g/cm$^3$ or more, and still more preferably 3.6 g/cm$^3$ or more. An upper limit thereof is preferably 4 g/cm$^3$ or less.

As a negative electrode active material for a lithium secondary battery, one or more selected from lithium metal, a lithium alloy, a carbon material capable of absorbing and releasing lithium [e.g., graphitizable carbon, non-graphitizable carbon having a spacing of a (002) plane of 0.37 nm or more, graphite having a spacing of the (002) plane of 0.34 nm or less, etc.], tin (elemental substance), a tin compound, silicon (elemental substance), a silicon compound, and a lithium titanate compound, such as $Li_4Ti_5O_{12}$, etc., may be used.

Among those, in the ability of absorbing and releasing a lithium ion, the use of a high-crystalline carbon material, such as artificial graphite, natural graphite, etc., is more preferred, and the use of a carbon material having a graphite-type crystal structure in which a lattice (002) spacing ($d_{002}$) is 0.340 nm (nanometers) or less, and especially from 0.335 to 0.337 nm, is especially preferred.

The use of artificial graphite particles having a bulky structure containing plural flattened graphite fine particles that are aggregated or bonded non-parallel to each other, or graphite particles produced through a spheroidizing treatment of flaky natural graphite particles by repeatedly applying a mechanical action, such as a compression force, a friction force, a shear force, etc., is preferred because when a ratio I(110)/I(004) of a peak intensity I(110) of the (110) plane to a peak intensity I(004) of the (004) plane of the graphite crystal obtained through X-ray diffractometry of a negative electrode sheet that is shaped under pressure to such an extent that a density of the negative electrode except for the collector is 1.5 g/cm$^3$ or more is 0.01 or more, the electrochemical characteristics are much more improved at a high temperature range. The ratio I(110)/I(004) is more preferably 0.05 or more, and still more preferably 0.1 or more. An upper limit thereof is preferably 0.5 or less, and more preferably 0.3 or less because there may be the case where the crystallinity is worsened to lower the discharge capacity of the battery due to an excessive treatment.

When the high-crystalline carbon material (core material) is coated with a carbon material having lower crystallinity than the core material, the electrochemical characteristics at a high temperature become much more favorable, and hence, such is preferred. The crystallinity of the carbon material in the coating may be confirmed through TEM.

When the high-crystalline carbon material is used, there is a tendency that it reacts with the nonaqueous electrolytic solution on charging, thereby worsening the electrochemical characteristics at a high temperature due to an increase of interfacial resistance. However, in the lithium secondary battery according to the present invention, the electrochemical characteristics at a high temperature become favorable.

Examples of the metal compound capable of absorbing and releasing lithium as a negative electrode active material include a compound containing at least one metal element, such as Si, Ge, Sn, Pb, P, Sb, Bi, Al, Ga, In, Ti, Mn, Fe, Co, Ni, Cu, Zn, Ag, Mg, Sr, Ba, etc. The metal compound may be in any form including an elemental substance, an alloy, an oxide, a nitride, a sulfide, a boride, an alloy with lithium, and the like, and any of an elemental substance, an alloy, an oxide, and an alloy with lithium is preferred because the battery capacity can be increased. Above all, a compound containing at least one element selected from Si, Ge, and Sn is preferred, and a compound containing at least one element selected from Si and Sn is more preferred because the battery capacity can be increased.

The negative electrode can be produced in such a manner that the same electroconductive agent, binder, and high-boiling point solvent as in the production of the positive electrode as described above are used and kneaded to provide a negative electrode mixture, and the negative electrode mixture is then applied on a collector, such as a copper foil, etc., dried, shaped under pressure, and then heat-treated in vacuum at a temperature of about 50° C. to 250° C. for about 2 hours.

A density of the negative electrode except for the collector is generally 1.1 g/cm$^3$ or more, and for the purpose of further increasing a capacity of the battery, the density is preferably 1.5 g/cm$^3$ or more, and especially preferably 1.7 g/cm$^3$ or more. An upper limit thereof is preferably 2 g/cm$^3$ or less.

Examples of the negative electrode active material for a lithium primary battery include lithium metal and a lithium alloy.

The structure of the lithium battery is not particularly limited, and may be a coin-type battery, a cylinder-type battery, a prismatic battery, a laminate-type battery, or the like, each having a single-layered or multi-layered separator.

The separator for the battery is not particularly limited, and a single-layered or laminated micro-porous film of a polyolefin, such as polypropylene, polyethylene, etc., a woven fabric, a nonwoven fabric, and the like may be used.

The lithium secondary battery in the present invention has excellent electrochemical characteristics at a high temperature even when a final charging voltage is 4.2 V or more, particularly 4.3 V or more, and furthermore, the characteristics are favorable even at 4.4 V or more. A final discharging voltage may be generally 2.8 V or more, and further 2.5 V or more, and the final discharging voltage of the lithium secondary battery in the present invention may be 2.0 V or more. An electric current is not particularly limited, and in general, the battery may be used within a range of from 0.1 to 30 C. The lithium battery in the present invention may be charged and discharged at from −40 to 100° C., and preferably from −10 to 80° C.

In the present invention, as a countermeasure against the increase in the internal pressure of the lithium battery, there may also be adopted such a method that a safety valve is provided in a battery cap, or a cutout is provided in a component, such as a battery can, a gasket, etc. As a safety countermeasure for prevention of overcharging, a circuit cut-off mechanism capable of detecting the internal pressure of the battery to cut off the current may be provided in the battery cap.

[Second Energy Storage Device (Electric Double Layer Capacitor)]

The second energy storage device of the present invention is an energy storage device including the nonaqueous electrolytic solution of the present invention and storing energy by utilizing an electric double layer capacitance in an interface between the electrolytic solution and the electrode. One example of the present invention is an electric double layer capacitor. A most typical electrode active material which is used in this energy storage device is active carbon. The double layer capacitance increases substantially in proportion to a surface area.

[Third Energy Storage Device]

The third energy storage device of the present invention is an energy storage device including the nonaqueous electrolytic solution of the present invention and storing energy by utilizing a doping/dedoping reaction of the electrode. Examples of the electrode active material which is used in this energy storage device include a metal oxide, such as ruthenium oxide, iridium oxide, tungsten oxide, molybdenum oxide, copper oxide, etc., and a π-conjugated polymer, such as polyacene, a polythiophene derivative, etc. A capacitor using such an electrode active material is capable of storing energy following the doping/dedoping reaction of the electrode.

[Fourth Energy Storage Device (Lithium Ion Capacitor)]

The fourth energy storage device of the present invention is an energy storage device including the nonaqueous electrolytic solution of the present invention and storing energy by utilizing intercalation of a lithium ion into a carbon material, such as graphite, etc., as the negative electrode. This energy storage device is called a lithium ion capacitor (LIC). As the positive electrode, there are suitably exemplified one utilizing an electric double layer between an active carbon electrode and an electrolytic solution, one utilizing a doping/dedoping reaction of a π-conjugated polymer electrode, and the like. The electrolytic solution contains at least a lithium salt, such as $LiPF_6$, etc.

[Phosphonoformic Acid Compound Represented by General Formula (III)]

The phosphonoformic acid compound having at least one alkynyl group, which is a novel compound of the present invention, is represented by the following general formula (III).

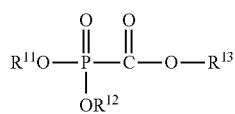

(III)

In the formula, each of $R^{11}$ to $R^{13}$ independently represents an aliphatic organic group having 1 to 5 carbon atoms, provided that at least one of $R^{11}$ to $R^{13}$ represents an alkynyl group having 3 to 5 carbon atoms.

In the general formula (III), the aliphatic organic group means an aliphatic functional group constituted of an atom selected from a carbon atom, a hydrogen atom, a nitrogen atom, an oxygen atom, and a halogen atom, as described above.

The aliphatic organic group having 1 to 5 carbon atoms, which is represented by $R^{11}$ to $R^{13}$, is preferably an alkyl group having 1 to 5 carbon atoms, an alkenyl group having 2 to 5 carbon atoms, or an alkynyl group having 3 to 5 carbon atoms.

Suitable examples of the alkyl group represented by $R^{11}$ to $R^{13}$ include a straight-chain alkyl group, such as a methyl group, an ethyl group, an n-propyl group, an n-butyl group, an n-pentyl group, etc., and a branched alkyl group, such as an isopropyl group, a sec-butyl group, a tert-butyl group, etc. The carbon number of the aforementioned alkyl group is more preferably 1 to 3, and specifically, a methyl group, an ethyl group, or an n-propyl group is more preferred, and a methyl group or an ethyl group is still more preferred.

Suitable examples of the alkenyl group represented by $R^{11}$ to $R^{13}$ include a straight-chain alkenyl group, such as a vinyl group, a 2-propenyl group, a 2-butenyl group, a 3-butenyl group, etc., and a branched alkenyl group, such as a 2-methyl-2-propenyl group, a 3-butene-2-yl group, 2-methyl-3-butene-2-yl group, a 3-methyl-2-butenyl group, etc. The carbon number of the aforementioned alkenyl group is more preferably 2 or 3, and specifically, a vinyl group or a 2-propenyl group is more preferred, and a 2-propenyl group is still more preferred.

Suitable examples of the alkynyl group represented by $R^{11}$ to $R^{13}$ include a straight-chain alkynyl group, such as a 2-propynyl group, a 2-butynyl group, a 3-butynyl group, a 2-pentynyl group, etc., and a branched alkynyl group, such as a 3-butyne-2-yl group, a 2-methyl-3-butyne-2-yl group, etc. The carbon number of the aforementioned alkynyl group is more preferably 3 or 4, and specifically, a 2-propynyl group or a 3-butynyl group is more preferred, and a 2-propynyl group is still more preferred.

In the general formula (III), at least one of $R^{11}$ to $R^{13}$ represents an alkynyl group having 3 to 5 carbon atoms. It is preferred that $R^{13}$ is an alkynyl group having 3 to 5 carbon atoms, and the case where all of $R^{11}$ to $R^{13}$ are an alkynyl group having 3 to 4 carbon atoms is more preferred.

Specific examples of the phosphonoformic acid compound having at least one alkynyl group, which is represented by the foregoing general formula (III), are the aforementioned Compounds B1 to B19 and B20 to B32.

Of the foregoing compounds, Compounds B1 to B19, B29, and B32 are preferred; Compounds B1 to B19 are more preferred; one or more selected from 2-propynyl (dimethoxyphosphoryl)formate (Compound B1), 2-propynyl (diethoxyphosphoryl)formate (Compound B2), 2-propynyl (ethoxymethoxyphosphoryl)formate (Compound B3), 2-propynyl (dipropyloxyphosphoryl)formate (Compound B4), 2-propynyl (dibutyloxyphosphoryl)formate (Compound B5), 2-butynyl (diethoxyphosphoryl)formate (Compound B9), 2-pentynyl (diethoxyphosphoryl)formate (Compound B11), 3-butyne-2-yl (diethoxyphosphoryl)formate (Compound B12), 2-methyl-3-butyne-2-yl (diethoxyphosphoryl)formate (Compound B13), 2-propynyl (bis(2-propynyloxy)phosphoryl)formate (Compound B14), 2-butynyl (bis(2-butynyloxy)phosphoryl)formate (Compound B15), 2-pentynyl (bis(2-pentynyloxy)phosphoryl)formate (Compound B17), 3-butyne-2-yl (bis(3-butyne-2-yloxy)phosphoryl)formate (Compound B18), 2-methyl-3-butyne-2-yl (bis (2-methyl-3-butyne-2-yloxy)phosphoryl)formate (Compound B19), and 2-propynyl (ethoxy(2-propynyloxy) phosphoryl)formate (Compound B29) are still more preferred; and one or more selected from 2-propynyl (dimethoxyphosphoryl)formate (Compound B1), 2-propynyl (diethoxyphosphoryl)formate (Compound B2), 2-propynyl (bis(2-propynyloxy)phosphoryl)formate (Compound B14), 2-butynyl (bis(2-butynyloxy)phosphoryl)formate (Compound B15), and 3-butyn-2-yl (bis(3-butyn-2-yloxy)phosphoryl)formate (Compound B18) are yet still more preferred.

The phosphonoformic acid compound having at least one alkynyl group according to the present invention may be synthesized by (a) a method of allowing an alkynyl chloroformate to react with a phosphite (hereinafter also referred to as "method (a)") or (b) a method of subjecting a phosphonoformate to transesterifying with an alkynyl alcohol in the presence or absence of a solvent and in the presence of a catalyst (hereinafter also referred to as "method (b)"). However, the present invention is not limited to these methods.

[Method (a)]

The method (a) is a method of allowing an alkynyl chloroformate to react with a phosphite. It is possible to synthesize the alkynyl chloroformate that is a raw material through an existent general-purpose technique. For example, the alkynyl chloroformate may be synthesized by a method of allowing phosgene or triphosgene to react with an alkynyl alcohol in the presence of a solvent.

As the alkynyl chloroformate which is used in the method (a), there are suitably exemplified 2-propynyl chloroformate, 2-butynyl chloroformate, 3-butynyl chloroformate, 2-pentynyl chloroformate, 1-methyl-2-propynyl chloroformate, 1,1-dimethyl-2-propynyl chloroformate, and the like. However, the alkynyl chloroformate is not limited thereto.

As the phosphite which is used in the method (a), there are suitably exemplified trimethyl phosphite, triethyl phosphite, tripropyl phosphite, tributyl phosphite, triisopropyl phosphite, tris(2-propenyl) phosphite, tris(2-butenyl) phosphite, tris(3-butenyl) phosphite, tris(2-methyl-2-propenyl) phosphite, tris(3-butene-2-yl) phosphite, tris(2-methyl-3-butene-2-yl) phosphite, tris(3-methyl-2-butenyl) phosphite, tris(2-propynyl) phosphite, tris(2-butynyl) phosphite, tris(3-butynyl) phosphite, tris(2-pentynyl) phosphite, tris(3-butyne-2-yl) phosphite, tris(2-methyl-3-butyne-2-yl) phosphite, and the like. However, the phosphite is not limited thereto.

In the method (a), an amount of the phosphite used is 0.8 to 20 mol, more preferably 0.9 to 10 mol, and still more preferably 1 to 5 mol per mol of the alkynyl chloroformate.

Although a solvent may be used in the method (a), from the viewpoint of a reaction rate, it is preferred to perform the reaction in the absence of a solvent.

In the method (a), from the viewpoint of not lowering the reactivity, a lower limit of a reaction temperature is preferably −20° C. or higher, and more preferably −10° C. or higher. From the viewpoint of suppressing side-reaction or decomposition of a product, an upper limit of the reaction temperature is preferably 100° C. or lower, and more preferably 80° C. or lower.

Although a reaction time may be properly varied according to the reaction temperature or scale, when the reaction time is too short, unreacted substances remain, and conversely, when the reaction time is too long, there is a concern about decomposition of a reaction product or side-reaction, and therefore, the reaction time is preferably 0.1 to 12 hours, and more preferably 0.2 to 6 hours.

[Method (b)]

The method (b) is a method of subjecting a phosphonoformate to transesterifying with a hydroxy compound in the presence or absence of a solvent and in the presence of a catalyst.

As the phosphonoformate which is used in the method (b), there are suitably exemplified methyl (diethoxyphosphoryl) formate, methyl (dimethoxyphosphoryl)formate, ethyl (diethoxyphosphoryl)formate, ethyl (dimethoxyphosphoryl) formate, propyl (diethoxyphosphoryl)formate, butyl (diethoxyphosphoryl)formate, 2-propenyl (diethoxyphosphoryl)formate, 2-propynyl (dimethoxyphosphoryl)formate, 2-propynyl (diethoxyphosphoryl)formate, and the like. However, the phosphonoformate is not limited thereto.

As the alkynyl alcohol which is used in the method (b), there are suitably exemplified 2-propyn-1-ol, 2-butyn-1-ol, 3-butyn-1-ol, 4-pentyn-1-ol, 5-hexyn-1-ol, 1-methyl-2-propyn-1-ol, 1,1-dimethyl-2-propyn-1-ol, and the like. However, the alkynyl alcohol is not limited thereto.

In the method (b), an amount of the alkynyl alcohol used is preferably 0.8 to 20 mol, more preferably 0.9 to 10 mol, and still more preferably 1 to 5 mol per mol of the phosphonoformate.

In the method (b), while the reaction proceeds in the absence of a solvent, a solvent may be used so long as it is inert against the reaction. Examples of the solvent used include an aliphatic hydrocarbon, a halogenated hydrocarbon, an aromatic hydrocarbon, a halogenated aromatic hydrocarbon, an ether, a nitrile, a sulfoxide, and a mixture thereof. Among those, an aliphatic or aromatic hydrocarbon which is hardly miscible with water, such as heptane, cyclohexane, toluene, etc., is preferred.

An amount of the solvent used is preferably 0 to 30 parts by mass, and more preferably 1 to 10 parts by mass per part by mass of the phosphonoformate.

In the method (b), any of an acid catalyst and a base catalyst may be used as the catalyst. Examples of the acid catalyst include a mineral acid, such as sulfuric acid, phosphoric acid, etc., a sulfonic acid, such as p-toluenesulfonic acid, methanesulfonic acid, trifluoromethanesulfonic acid, etc., a Lewis acid, such as trifluoroboric acid, tetraethoxy titanium, tetraisopropoxy titanium, etc., a solid acid, such as zeolite, an acidic resin, etc., and a mixture thereof. Among those, phosphoric acid, p-toluenesulfonic acid, methanesulfonic acid, trifluoromethanesulfonic acid, tetraethoxy titanium, tetraisopropoxy titanium, and the like are preferred. Examples of the base catalyst include an alkali metal carbonate, such as sodium carbonate, potassium carbonate, etc., an alkali metal alcoholate, such as sodium methylate, sodium ethylate, potassium tert-butoxide, etc., an alkali metal hydride, such as sodium hydride, potassium hydride, etc., an alkali metal, such as sodium, potassium, lithium, etc., and a mixture thereof. Among those, an alkali metal carbonate, such as sodium carbonate, potassium carbonate, etc., is preferred.

From the viewpoint of suppressing side-reaction, an amount of the catalyst used is preferably 0.001 to 5 mol, more preferably 0.005 to 1 mol, and still more preferably 0.01 to 0.3 mol per mol of the phosphonoformate.

In the method (b), a lower limit of a reaction temperature is preferably 0° C. or higher, and in order that the reactivity may not be lowered, the reaction temperature is preferably 20° C. or higher. An upper limit of the reaction temperature is preferably 200° C. or lower, and in order to suppress side-reaction or decomposition of a product, the reaction temperature is more preferably 150° C. or lower. Although a reaction time is varied according to the reaction temperature or scale, when the reaction time is too short, unreacted substances remain, and conversely, when the reaction time is too long, side-reaction or decomposition of a product is liable to proceed, and therefore, the reaction time is preferably 0.1 to 24 hours, and more preferably 0.2 to 15 hours.

EXAMPLES

Synthesis Examples of the phosphonoformic acid compound and Examples of the electrolytic solution using the phosphonoformic acid compound are hereunder described, but it should not be construed that the present invention is limited to these Examples.

Synthesis Example 1 [Synthesis of 2-propynyl (dimethoxyphosphoryl)formate (Compound B1)]

To 2.59 g (21.9 mmol) of 2-propynyl chloroformate, 3.53 g (28.5 mmol) of trimethyl phosphite was added dropwise at room temperature over 15 minutes, and after stirring for 1 hour, the resultant was concentrated under reduced pressure. A residue obtained by removing the excessive trimethyl phosphite was purified by means of silica gel column chromatography (elution with ethyl acetate/hexane=1/2), thereby obtaining 1.02 g of the targeted 2-propynyl (dimethoxyphosphoryl)formate as a colorless oily material (yield: 24%).

The obtained 2-propynyl (dimethoxyphosphoryl)formate was subjected to measurement of $^1$H-NMR, thereby confirming its structure.

(1) $^1$H-NMR (400 MHz, CDCl$_3$): δ=4.85 (d, J=2.5 Hz, 2H), 3.95 (d, J=11.2 Hz, 6H), 2.61 (t, J=2.5 Hz, 1H)

Synthesis Example 2 [Synthesis of 2-propynyl (diethoxyphosphoryl)formate (Compound B2)]

To 5.00 g (42.2 mmol) of 2-propynyl chloroformate, 7.72 g (46.5 mmol) of triethyl phosphite was added dropwise at room temperature over 30 minutes, and after stirring for 1 hour, the resultant was concentrated under reduced pressure. A residue obtained by removing the excessive triethyl phosphite was purified by means of silica gel column chromatography (elution with ethyl acetate/hexane=1/2), thereby obtaining 8.20 g of the targeted 2-propynyl (diethoxyphosphoryl)formate as a colorless oily material (yield: 88%).

The obtained 2-propynyl (diethoxyphosphoryl)formate was subjected to measurements of $^1$H-NMR and mass spectrometry, thereby confirming its structure.

(1) $^1$H-NMR (400 MHz, CDCl$_3$): δ=4.83 (d, J=2.5 Hz, 2H), 4.38 to 4.26 (m, 4H), 2.55 (t, J=2.5 Hz, 1H), 1.41 (dt, J=0.5, 7.1 Hz, 6H)

(2) Mass spectrometry: MS (EI) m/z (%)=220 (0.4)[M$^+$], 165 (1), 137 (36), 109 (100), 91 (20), 81 (66), 39 (25), 29 (22)

(3) Mass spectrometry: MS (CI) m/z=221 [M+1]$^+$

Synthesis Example 3 [Synthesis of 2-propynyl (ethoxy(2-propynyloxy)phosphoryl)formate (Compound B29) and 2-propynyl (bis(2-propynyloxy) phosphoryl)formate (Compound B14)]

In a reactor equipped with a distillation unit, 10.00 g (45.4 mmol) of 2-propynyl (diethoxyphosphoryl)formate obtained in Synthesis Example 2, 12.73 g (227.1 mmol) of 2-propyn-1-ol, and 0.09 g (0.9 mmol) of phosphoric acid were added and stirred at a bath temperature of 100° C. for 2 hours. The pressure was reduced to 270 Torr while keeping the bath temperature, followed by transesterifying for 10 hours while distilling off ethanol. A residue obtained by concentration under reduced pressure was purified by means of silica gel column chromatography (elution with ethyl acetate/ hexane=1/4), 3.81 g of 2-propynyl (diethoxyphosphoryl) formate that is the raw material was recovered, and 3.34 g (yield: 32%) of 2-propynyl (ethoxy(2-propynyloxy)phosphoryl)formate and 1.96 g (yield: 18%) of 2-propynyl (bis (2-propynyloxy)phosphoryl)formate were obtained as a pale yellow oily material, respectively.

The obtained 2-propynyl (ethoxy(2-propynyloxy)phosphoryl)formate and 2-propynyl (bis(2-propynyloxy)phosphoryl)formate were subjected to measurement of mass spectrometry, thereby confirming their structures.

2-Propynyl (ethoxy(2-propynyloxy)phosphoryl)formate (1) Mass spectrometry: MS (EI) m/z (%)=147 (16), 119 (98), 39 (100)

(2) Mass spectrometry: MS (CI) m/z=231 [M+1]$^+$

2-Propynyl (bis(2-propynyloxy)phosphoryl)formate (1) Mass spectrometry: MS (EI) m/z (%)=201 (0.2), 157 (6), 117 (10), 94 (11), 65 (14), 39 (100)

(2) Mass spectrometry: MS (CI) m/z=241 [M+1]$^+$

Examples 1 to 28 and Comparative Examples 1 to 3

[Production of Lithium Ion Secondary Battery]

94% by mass of LiNi$_{1/3}$Mn$_{1/3}$Co$_{1/3}$O$_2$ (positive electrode active material) and 3% by mass of acetylene black (electroconductive agent) were mixed and then added to and mixed with a solution which had been prepared by dissolving 3% by mass of polyvinylidene fluoride (binder) in 1-methyl-2-pyrrolidone in advance, thereby preparing a positive electrode mixture paste. This positive electrode mixture paste was applied onto one surface of an aluminum foil (collector), dried, and treated under pressure, followed by cutting into a predetermined size, thereby producing a positive electrode sheet in a belt-like form.

10% by mass of silicon (elemental substance, negative electrode active material), 80% by mass of artificial graphite (d$_{002}$=0.335 nm, negative electrode active material), and 5% by mass of acetylene black (electroconductive agent) were mixed and then added to and mixed with a solution which had been prepared by dissolving 5% by mass of polyvinylidene fluoride (binder) in 1-methyl-2-pyrrolidone in advance, thereby preparing a negative electrode mixture paste. This negative electrode mixture paste was applied onto one surface of a copper foil (collector), dried, and treated under pressure, followed by cutting into a predetermined size, thereby producing a negative electrode sheet.

The above-obtained positive electrode sheet, a microporous polyethylene-made film separator, and the above-obtained negative electrode sheet were laminated in this order, and a nonaqueous electrolytic solution having each of compositions shown in Tables 1 to 4 was added, thereby producing a laminate-type battery.

The obtained batteries were evaluated by the following methods. The results are shown in Tables 1 to 4.

[Evaluation of High-Temperature Cycle Properties]

In a thermostatic chamber at 45° C., each of the batteries produced by the aforementioned method was treated by repeating a cycle of charging up to a final voltage of 4.3 V with a constant current of 1.5 C and under a constant voltage for 3 hours and subsequently discharging down to a discharge voltage of 3.0 V with a constant current of 1 C, until it reached 200 cycles. Then, a discharge capacity retention rate after 200 cycles was determined according to the following equation.

Discharge capacity retention rate (%)=(Discharge capacity after 200 cycles)/(Discharge capacity after 1st cycle)×100

[Evaluation of Heat Stability of Negative Electrode]

Each of the batteries after the cycle properties evaluation was discharged down to a discharge voltage of 3.0 V at 25° C. with a constant current of 0.2 C and under a constant voltage and subsequently charged for 3 hours up to a final voltage of 4.3 V with a constant current 0.2 C and under a constant voltage. The battery after charging was disassembled, and the negative electrode was washed with dimethyl carbonate. Then, the negative electrode was cut such that a weight of the negative electrode active material was 1 mg, and the resulting cut piece of the negative electrode was enclosed in an SUS pan together with 1 mg of a nonaqueous electrolytic solution. 1.2M LiPF$_6$ (EC/PC/MEC/DEC=26/4/30/40) was used as the nonaqueous electrolytic solution.

This SUS pan was subjected to the measurement of differential scanning calorimetry (DSC) with a differential scanning calorimeter (a trade name: TAS300, manufactured by Rigaku Corporation) in an argon atmosphere at a temperature rise rate of 10° C./min within a range of from ambient temperature to 400° C. An amount of heat generation (J/g) at 100° C. to 300° C. per gram of the negative electrode active material in a charged state was calculated from the results, and a relative amount of heat generation (heat stability) was evaluated while defining the amount of heat generation of Comparative Example 1 as 100%.

TABLE 1

| | Composition of electrolyte salt Composition of nonaqueous electrolytic solution (Volume ratio of solvent) | Compound of general formula (I) or (II) (% by mass) | Discharge capacity retention rate after 200 cycles at 45° C. (%) | Relative value of the amount of heat generation of negative electrode (%) |
|---|---|---|---|---|
| Example 1 | 1.2 M LiPF$_6$ EC/PC/MEC/DEC (26/4/30/40) | 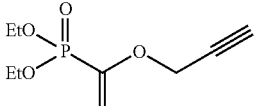 (1) | 70 | 54 |
| Example 2 | 1.2 M LiPF$_6$ EC/PCNC/MEC/DEC (26/3/1/30/40) | 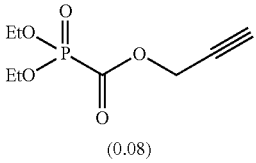 (0.08) | 73 | 51 |
| Example 3 | 1.2 M LiPF$_6$ EC/PCNC/MEC/DEC (26/3/1/30/40) | 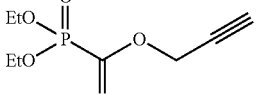 (0.3) | 75 | 49 |
| Example 4 | 1.2 M LiPF$_6$ EC/PCNC/MEC/DEC (26/3/1/30/40) | 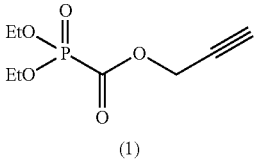 (1) | 76 | 41 |
| Example 5 | 1.2 M LiPF$_6$ EC/PCNC/MEC/DEC (26/3/1/30/40) | 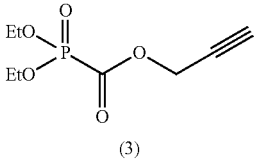 (3) | 73 | 46 |
| Example 6 | 1.2 M LiPF$_6$ EC/PCNC/MEC/DEC (26/3/1/30/40) | 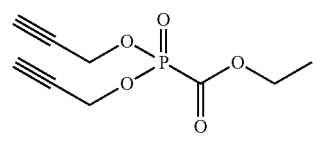 (1) | 73 | 46 |
| Example 7 | 1.2 M LiPF$_6$ EC/PCNC/MEC/DEC (26/3/1/30/40) | 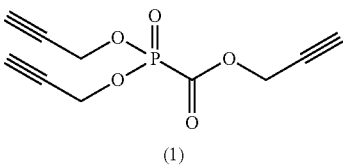 [SMILES: C#CCOC(=O)P(=O)(OCC#C)OCC#C] (1) | 77 | 40 |

TABLE 1-continued

| | Composition of electrolyte salt Composition of nonaqueous electrolytic solution (Volume ratio of solvent) | Compound of general formula (I) or (II) (% by mass) | Discharge capacity retention rate after 200 cycles at 45° C. (%) | Relative value of the amount of heat generation of negative electrode (%) |
|---|---|---|---|---|
| Example 8 | 1.2 M LiPF$_6$ EC/PCNC/MEC/DEC (26/3/1/30/40) | 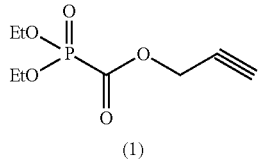 (1) | 75 | 43 |
| Example 9 | 1.2 M LiPF$_6$ EC/PCNC/MEC/DEC (26/3/1/30/40) | 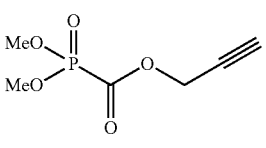 (1) | 75 | 41 |
| Example 10 | 1.2 M LiPF$_6$ EC/PC/FEC/ VC/MEC/DEC/DMC (25/1/3/1/30/20/20) | 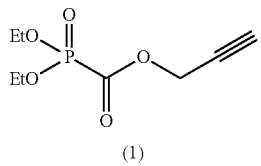 (1) | 78 | 39 |
| Comparative Example 1 | 1.2 M LiPF$_6$ EC/PCNC/MEC/DEC (26/3/1/30/40) | None | 59 | 100 |
| Comparative Example 2 | 1.2 M LiPF$_6$ EC/PCNC/MEC/DEC (26/3/1/30/40) | 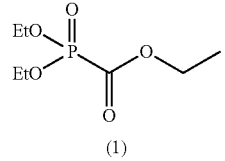 (1) | 62 | 81 |
| Comparative Example 3 | 1.2 M LiPF$_6$ EC/PCNC/MEC/DEC (26/3/1/30/40) | 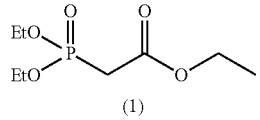 (1) | 63 | 77 |

TABLE 2

| | Composition of electrolyte salt Composition of nonaqueous electrolytic solution (Volume ratio of solvent) | Compound of general formula (I) or (II) (% by mass) | Discharge capacity retention rate after 200 cycles at 45° C. (%) | Relative value of the amount of heat generation of negative electrode (%) |
|---|---|---|---|---|
| Example 11 | 1.2 M LiPF$_6$ EC/PCNC/MEC/DEC (26/3/1/30/40) | 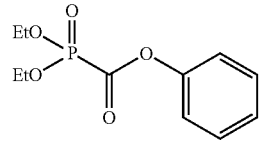 (1) | 78 | 39 |
| Example 12 | 1.2 M LiPF$_6$ EC/PCNC/MEC/DEC (26/3/1/30/40) | 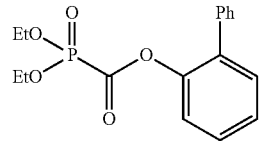 (1) | 77 | 40 |

TABLE 2-continued

| | Composition of electrolyte salt Composition of nonaqueous electrolytic solution (Volume ratio of solvent) | Compound of general formula (I) or (II) (% by mass) | Discharge capacity retention rate after 200 cycles at 45° C. (%) | Relative value of the amount of heat generation of negative electrode (%) |
|---|---|---|---|---|
| Example 13 | 1.2 M LiPF$_6$ EC/PCNC/MEC/DEC (26/3/1/30/40) | 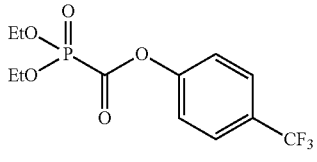 (1) | 76 | 38 |
| Example 14 | 1.2 M LiPF$_6$ EC/PCNC/MEC/DEC (26/3/1/30/40) | 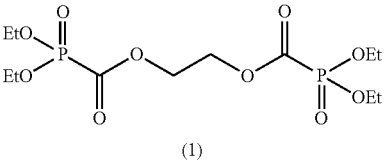 [SMILES: CCOP(=O)(OCC)C(=O)OCCOC(=O)P(=O)(OCC)OCC] (1) | 76 | 39 |
| Example 15 | 1.2 M LiPF$_6$ EC/PCNC/MEC/DEC (26/3/1/30/40) | 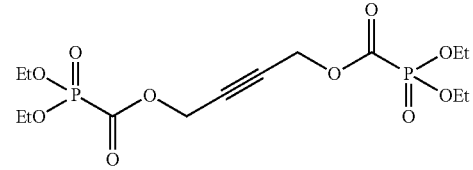 (1) | 79 | 36 |
| Example 16 | 1.2 M LiPF$_6$ EC/PCNC/MEC/DEC (26/3/1/30/40) + Adiponitrile (1 wt %) + LiPO$_2$F$_2$ (0.3 wt %) | 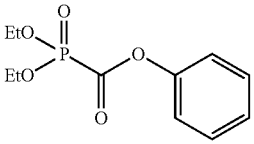 (1) | 82 | 34 |

TABLE 3

| | Composition of electrolyte salt Composition of nonaqueous electrolytic solution (Volume ratio of solvent) | Compound of general formula (I) or (II) | | Compound used in combination with the compound of general formula (I) or (II) | | Discharge capacity retention rate after 200 cycles at 45° C. (%) | Relative value of the amount of heat generation of negative electrode (%) |
|---|---|---|---|---|---|---|---|
| | | Kind | Addition amount (Content in nonaqueous electrolytic solution) (% by mass) | Kind | Addition amount (Content in nonaqueous electrolytic solution) (% by mass) | | |
| Example 17 | 1.2 M LiPF$_6$ EC/PCNC/MEC/DEC (26/3/1/30/40) | 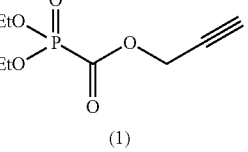 (1) | 0.3 | 1,3-Dioxane | 2 | 80 | 37 |
| Example 18 | 1.2 M LiPF$_6$ EC/PCNC/MEC/DEC (26/3/1/30/40) | | 0.5 | | 1 | 81 | 35 |
| Example 19 | 1.2 M LiPF$_6$ EC/PCNC/MEC/DEC (26/3/1/30/40) | | 2 | | 0.5 | 79 | 36 |
| Example 20 | 1.2 M LiPF$_6$ EC/PCNC/MEC/DEC (26/3/1/30/40) | | 1 | Hexamethylene diisocyanate + Adiponitrile | 1 + 1 | 82 | 34 |

TABLE 3-continued

| | Composition of electrolyte salt Composition of nonaqueous electrolytic solution (Volume ratio of solvent) | Compound of general formula (I) or (II) | | Compound used in combination with the compound of general formula (I) or (II) | | Discharge capacity retention rate after 200 cycles at 45° C. (%) | Relative value of the amount of heat generation of negative electrode (%) |
|---|---|---|---|---|---|---|---|
| | | Kind | Addition amount (Content in nonaqueous electrolytic solution) (% by mass) | Kind | Addition amount (Content in nonaqueous electrolytic solution) (% by mass) | | |
| Example 21 | 1.2 M LiPF$_6$ EC/PCNC/MEC/DEC (26/3/1/30/40) | 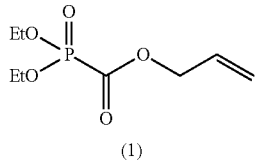 (1) | 0.5 | 1,3-Dioxane | 1 | 78 | 36 |
| Example 22 | 1.2 M LiPF$_6$ EC/PCNC/MEC/DEC (26/3/1/30/40) |  | 0.3 | Methyl phenyl carbonate | 2 | 80 | 36 |
| Example 23 | 1.2 M LiPF$_6$ EC/PCNC/MEC/DEC (26/3/1/30/40) | | 0.5 | | 1 | 81 | 34 |
| Example 24 | 1.2 M LiPF$_6$ EC/PCNC/MEC/DEC (26/3/1/30/40) | | 2 | | 0.5 | 79 | 35 |

TABLE 4

| | Composition of electrolyte salt Composition of nonaqueous electrolytic solution (Volume ratio of solvent) | Compound of general formula (I) or (II) | | Second lithium salt | | Discharge capacity retention rate after 200 cycles at 45° C. (%) | Relative value of the amount of heat generation of negative electrode (%) |
|---|---|---|---|---|---|---|---|
| | | Kind | Addition amount (Content in nonaqueous electrolytic solution) (% by mass) | Kind | Addition amount (Content in nonaqueous electrolytic solution) (% by mass) | | |
| Example 25 | 1.2 M LiPF$_6$ EC/PCNC/MEC/DEC (26/3/1/30/40) | 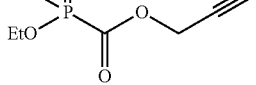 (1) | 0.5 | Lithium ethyl sulfate | 1 | 81 | 32 |
| Example 26 | 1.2 M LiPF$_6$ EC/PCNC/MEC/DEC (26/3/1/30/40) | | 1 | | 0.3 | 83 | 33 |
| Example 27 | 1.2 M LiPF$_6$ EC/PCNC/MEC/DEC (26/3/1/30/40) | | 1 | Lithium fluorosulfonate | 0.3 | 80 | 36 |
| Example 28 | 1.2 M LiPF$_6$ EC/PCNC/MEC/DEC (26/3/1/30/40) | | 1 | LiDFOB | 0.3 | 79 | 34 |

From Tables 1 to 4, all of the lithium secondary batteries of Examples 1 to 28 are conspicuously improved in the charging and discharging cycle properties at a high temperature and further particularly under a high voltage even at a rate of 1.5 C, as compared with the lithium secondary battery of Comparative Example 1 in which the specified phosphonoformic acid compound according to the present invention was not added, the lithium secondary battery of Comparative Example 2 using the nonaqueous electrolytic solution having triethyl phosphonoformate added thereto and the lithium secondary battery of Comparative Example 3 using the nonaqueous electrolytic solution having triethyl phosphonoacetate added thereto, as described in PTLs 1 to 3. In addition, it is noted that Examples 1 to 28 are smaller in the amount of heat generation of the negative electrode after 200 cycles than Comparative Examples 1 to 3.

In addition, the nonaqueous electrolytic solution in which the specified phosphonoformic acid compound according to the present invention is added similarly forms a surface film with high heat stability on a negative electrode of a lithium primary battery, such as lithium metal, etc., and therefore, it has been noted that even in the case of storing the lithium primary battery at a high temperature, the capacity is hardly lowered.

In the light of the above, it has become clear that the effect of the present invention is a peculiar effect in the case where a nonaqueous electrolytic solution having an electrolyte salt dissolved in a nonaqueous solvent contains a phosphonoformic acid compound having a specified substituent according to the present invention, namely at least one carbon-carbon unsaturated bond or two phosphonocarbonyl groups.

INDUSTRIAL APPLICABILITY

By using the nonaqueous electrolytic solution of the present invention, an energy storage device with excellent electrochemical characteristics at a high temperature can be obtained. In particular, when the nonaqueous electrolytic solution of the present invention is used as a nonaqueous electrolytic solution for an energy storage device to be mounted on a device having high possibility to be used at a high temperature, such as a hybrid electric vehicle, a plug-in hybrid electric vehicle, a battery electric vehicle, a tablet device, an ultrabook, etc., or the like, an energy storage device which is hardly worsened in electrochemical characteristics at a high temperature, in particular high-load charging and discharging cycle properties at a high temperature and further improved in heat stability of a negative electrode and improved in safety can be obtained.

In addition, the phosphonoformic acid compound having at least one alkynyl group, which is represented by the general formula (III), is not only useful as an additive for a lithium battery but also usable as an intermediate raw material of a drug, an agricultural chemical, an electronic material, a polymer material, and the like.

Furthermore, the nonaqueous electrolytic solution of the present invention can also be utilized as a nonaqueous electrolytic solution for other material than the energy storage device, such as a nonaqueous electrolytic solution for electrolysis, a nonaqueous electrolytic solution for electroplating, etc.

The invention claimed is:

1. A nonaqueous electrolytic solution comprising:
an electrolyte salt dissolved in a nonaqueous solvent, and
0.001 to 5% by mass of at least one phosphonoformic acid compound having at least one carbon-carbon unsaturated bond, which is represented by a formula (I):

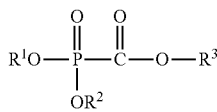
(I)

wherein each of $R^1$ to $R^3$ independently represents an aliphatic organic group having 1 to 5 carbon atoms, provided that at least one of $R^1$ to $R^3$ represents a 2-propenyl group or a 2-propynyl group.

2. The nonaqueous electrolytic solution according to claim 1, comprising the phosphonoformic acid compound represented by formula (I), wherein in the formula (I), $R^3$ is a 2-propenyl group or a 2-propynyl group and each of $R^1$ and $R^2$ is independently an alkyl group having 1 to 4 carbon atoms or an alkynyl group having 3 to 5 carbon atoms.

3. The nonaqueous electrolytic solution according to claim 1, comprising at least one phosphonoformic acid compound represented by the formula (I) selected from the group consisting of 2-propynyl (dimethoxyphosphoryl)formate, 2-propynyl (diethoxyphosphoryl)formate, 2-propynyl (bis(2-propynyloxy)phosphoryl)formate, and 2-propenyl (diethoxyphosphoryl)formate.

4. The nonaqueous electrolytic solution according to claim 1, wherein the nonaqueous solvent comprises a cyclic carbonate and a linear ester.

5. The nonaqueous electrolytic solution according to claim 4, wherein the cyclic carbonate comprises one or more carbonates selected from the group consisting of ethylene carbonate, propylene carbonate, 1,2-butylene carbonate, and 2,3-butylene carbonate.

6. The nonaqueous electrolytic solution according to claim 4, wherein the cyclic carbonate comprises a cyclic carbonate having a fluorine atom or an unsaturated bond.

7. The nonaqueous electrolytic solution according to claim 4, wherein the linear ester comprises both a symmetric linear carbonate and an asymmetric linear carbonate, and a content of the symmetric linear carbonate is more than a content of the asymmetric linear carbonate.

8. The nonaqueous electrolytic solution according to claim 7, wherein the asymmetric linear carbonate is one or more carbonates selected from the group consisting of methyl ethyl carbonate, methyl propyl carbonate, methyl isopropyl carbonate, methyl butyl carbonate, and ethyl propyl carbonate.

9. The nonaqueous electrolytic solution according to claim 1, further comprising one or more compounds selected from the group consisting of an S(=O) group-containing compound, a fluorinated benzene compound, a carbon-carbon triple bond-containing compound, a carboxylic acid anhydride, a cyclic acetal compound, an isocyanate compound, a nitrile compound, a benzene compound, and a phosphazene compound.

10. The nonaqueous electrolytic solution according to claim 1, wherein the electrolyte salt comprises one or more lithium salts selected from the group consisting of $LiPF_6$, $LiBF_4$, $LiN(SO_2CF_3)_2$, and $LiN(SO_2F)_2$.

11. The nonaqueous electrolytic solution according to claim 10, wherein the electrolyte salt further comprises one or more lithium salts selected from the group consisting of an $S(=O)_2O$ structure-containing lithium salt, a P=O structure-containing lithium salt, and a lithium salt having a boron-containing oxalate complex as an anion.

12. The nonaqueous electrolytic solution according to claim 1, which is suitable for use in an energy storage device.

13. An energy storage device comprising:
a positive electrode,
a negative electrode, and
a nonaqueous electrolytic solution,
wherein the nonaqueous electrolytic solution comprises an electrolyte salt dissolved in a nonaqueous solvent, and 0.001 to 5% by mass of at least one phosphonoformic acid compound having at least one carbon-carbon unsaturated bond, which is represented by a formula (I):

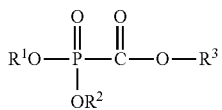
(I)

wherein each of $R^1$ to $R^3$ independently represents an aliphatic organic group having 1 to 5 carbon atoms, provided that at least one of $R^1$ to $R^3$ represents a 2-propenyl group or a 2-propynyl group.

14. The energy storage device according to claim 13, wherein an active material of the positive electrode is:
a complex metal oxide comprising lithium and one or more elements selected from the group consisting of cobalt, manganese, and nickel, or a lithium-containing olivine-type phosphate comprising one or more elements selected from the group consisting of iron, cobalt, nickel, and manganese.

15. The energy storage device according to claim 13, wherein an active material of the negative electrode comprises one or more members selected from the group consisting of lithium metal, a lithium alloy, a carbon material capable of absorbing and releasing lithium, tin, a tin compound, silicon, a silicon compound, and a lithium titanate compound.

* * * * *